US006438419B1

(12) United States Patent
Callaway et al.

(10) Patent No.: US 6,438,419 B1
(45) Date of Patent: Aug. 20, 2002

(54) METHOD AND APPARATUS EMPLOYING A SCALING EXPONENT FOR SELECTIVELY DEFIBRILLATING A PATIENT

(75) Inventors: Clifton W. Callaway, Pittsburgh; Lawrence D. Sherman, Aspinwall, both of PA (US)

(73) Assignee: The University of Pittsburgh, Pittsburgh, PA (US)

(*) Notice: Subject to any disclaimer, the term of this patent is extended or adjusted under 35 U.S.C. 154(b) by 0 days.

(21) Appl. No.: 09/672,647

(22) Filed: Sep. 28, 2000

(51) Int. Cl.[7] .............................................. A61N 1/39
(52) U.S. Cl. ............................................ 607/5; 600/508
(58) Field of Search ................................ 600/508, 509, 600/515, 518; 607/4–8, 142

(56) References Cited

U.S. PATENT DOCUMENTS

| | | | |
|---|---|---|---|
| 4,114,628 A | | 9/1978 | Rizk |
| 5,077,667 A | * | 12/1991 | Brown et al. ................ 600/518 |
| 5,643,325 A | * | 7/1997 | Karagueuzian et al. ......... 607/8 |
| 5,676,690 A | | 10/1997 | Norén |
| 5,957,856 A | * | 9/1999 | Weil et al. .................... 600/518 |
| 5,999,852 A | * | 12/1999 | Elabbady et al. ............... 607/8 |
| 6,144,877 A | * | 11/2000 | DePetrillo .................... 600/515 |

OTHER PUBLICATIONS

Eisenberg, M., et al., Paramedic programs and out–of–hospital cardiac arrest: I. Factors associated with successful resuscitation, *American Journal of Public Health*, 1979, vol. 69, pp. 30–38.

Eisenberg, M., et al., Treatment of out–of–hospital cardiac arrest with rapid defibrillation by emergency medical technicians, *New England Journal of Medicine*, 1980, vol. 302, pp. 1379–1383.

Roth, R., et al., Out–of–hospital cardiac arrest: factors associated with survival, *Annals of Emergency Medicine*, 1984, vol. 13, pp. 237–243.

Auble, T., et al., Effect of out–of–hospital defibrillation by basic life support providers on cardiac arrest mortality: a metaanalysis, *Annals of Emergency Medicine*, 1995, vol. 25, pp. 642–648.

Stiell, I., et al., Improved out–of–hospital cardiac arrest survival through the inexpensive optimization of an existing defibrillation program: OPALS study phase II, *JAMA*, 1999, vol. 281, pp. 1175–1181.

(List continued on next page.)

*Primary Examiner*—Kennedy Schaetzle
*Assistant Examiner*—Kristen Droesch
(74) *Attorney, Agent, or Firm*—Kirk D. Houser; Arnold B. Silverman; Eckert Seamans Cherin & Mellott, LLC

(57) ABSTRACT

A defibrillator, which selectively delivers a defibrillation pulse to a patient, includes electrodes adapted for placement on the patient, a monitoring circuit for providing an electrocardiogram (ECG) of the patient, and a defibrillation pulse generator having an energy store for delivering a defibrillation pulse. A switch in electrical communication with the ECG monitoring circuit and the defibrillation pulse generator selectively electrically connects the monitoring circuit and the defibrillation pulse generator to the electrodes. A microprocessor is in electrical communication with the monitoring circuit, the defibrillation pulse generator, and the switch. The microprocessor causes the switch to electrically connect the monitoring circuit to the electrodes in order to provide the ECG of the patient. The microprocessor also determines a scaling exponent for the patient from the ECG thereof. The microprocessor further compares the scaling exponent to a predetermined value and selectively causes the switch to electrically connect the defibrillation pulse generator to the electrodes in order that the energy store delivers the defibrillation pulse to the patient.

38 Claims, 9 Drawing Sheets

OTHER PUBLICATIONS

Cobb, L., et al., Influence of cardiopulmonary resuscitation prior to defibrillation in patients with out–of–hospital ventricular fibrillation, *JAMA*, 1999, vol. 281, pp. 1182–1188.

Brown, C., et al., "Estimating the duration of ventricular fibrillation," *Annals of Emergency Medicine*, 1989, vol. 18, pp. 1181–1185.

Martin, D., et al., "Frequency analysis of the human and swine electrocardiogram during ventricular fibrillation," *Resuscitation*, 1991, vol. 22, pp. 85–91.

Callaham, M., et al., Prehospital cardiac arrest treated by urban first–responders: profile of patient response and prediction of outcome by ventricular fibrillation waveform, *Annals of Emergency Medicine*, 1993, vol. 22, pp. 1664–1677.

Weaver, W., et al., Amplitude of ventricular fibrillation waveform and outcome after cardiac arrest, *Annals of Internal Medicine*, 1985, vol. 102, pp. 53–55.

Brown, C., et al., Signal analysis of the human ECG during ventricular fibrillation: frequency and amplitude parameters as predictors of successful countershock, *Annals of Emergency Medicine*, 1996, vol. 27, pp. 184–188.

Strohmenger, H., et al., Frequency of ventricular fibrillation as a predictor of defibrillation success during cardiac surgery, *Anesthesia Analgesia*, 1994, vol. 79, pp. 434–438.

Hargarten, K., et al., Prehospital experience with defibrillation of coarse ventricular fibrillation: a ten–year review, *Annals of Emergency Medicine*, 1990, vol. 19, pp. 157–162.

Gaba, D., et al. Internal countershock produces myocardial damage and lactate production without myocardial ischemia in anesthetized dogs, *Anesthesiology*, 1987, vol. 66, pp. 477–482.

Ehsani, A., et al., Effects of electrical countershock on serum creatine phosphokinase (CPK) isoenzyme activity, *American Journal of Cardiology*, 1976, vol. 37, pp. 12–18.

Bardy, G., et al., Prospective evaluation of initially ineffective defibrillation pulses on defibrillation success during ventricular fibrillation in survivors of cardiac arrest, *American Journal of Cardiology*, 1988, vol. 62, pp. 718–722.

Bardy, G., et al., Arrhythmias/pacing/heart block: multicenter comparison of truncated biphasic shocks and standard damped sine wave monophasic shocks for transthoracic ventricular defibrillation, *Circulation*, 1996, vol. 94, pp. 2507–2514.

Niemann, J., et al., Treatment of prolonged ventricular fibrillation immediate countershock versus high–dose epinephrine and CPR preceding countershock, *Circulation*, 1992, vol. 85, pp. 281–287.

Barton, C., et al., Effect of selective aortic arch perfusion on median frequency and peak amplitude of ventricular fibrillation in a canine model, *Annals of Emergency Medicine*, 1996, vol. 27, pp. 610–616.

Strohmenger, H., et al., Effects of epinephrine and vasopressin on median fibrillation frequency and defibrillation success in a porcine model of cardiopulmonary resuscitation, *Resuscitation*, 1996, vol. 31, pp. 65–73.

Callaway, C. et al., Geometric Structure of Prolonged Ventricular Fibrillation in Swine, Mid–Year Meeting Abstracts from Department of Emergency Medicine, University of Pittsburgh Medical Center, Pittsburgh, Pennsylvania, 1998, 17 pages.

Callaway, C. et al., Scaling Structure of Electrocardiographic Waveform During Prolonged Ventricular Fibrillation in Swine, *PACE*, Feb. 2000, vol. 23, pp. 180–191.

\* cited by examiner

METHOD AND APPARATUS EMPLOYING A SCALING EXPONENT FOR SELECTIVELY DEFIBRILLATING A PATIENT

BACKGROUND OF THE INVENTION

1. Field of the Invention

The invention is directed to methods and apparatus for delivering defibrillating energy to a patient and, in particular, to methods and apparatus for selectively delivering defibrillating energy to patients.

2. Description of the Prior Art

Ventricular fibrillation (VF) is the most common initial arrhythmia associated with sudden cardiac death, and is one of the most common life-threatening medical conditions that occurs with respect to the human heart. In ventricular fibrillation, the human heart's electrical activity becomes unsynchronized, which results in a loss of its ability to contract. As a result, a fibrillating heart immediately loses its ability to pump blood into the circulation system.

Electrical defibrillation remains the mainstay of therapy for VF. A common treatment for ventricular fibrillation is to apply an electric pulse to the heart that is strong enough to stop the unsynchronized electrical activity and give the heart's natural pacemaker a chance to reinitiate a synchronized rhythm. External defibrillation is the method of applying the electric pulse to the fibrillating heart through a patient's thorax. See, for example, U.S. Pat. No. 5,999,852.

Existing external cardiac defibrillators first accumulate a high-energy electric charge in an energy store, typically a capacitor. When a switching mechanism is activated, the stored energy is applied to the patient via electrodes positioned on the patient's thorax. The resultant discharge of the capacitor causes a large current pulse to be transferred through the patient.

The current practice of resuscitation relies on visual inspection of the electrocardiogram (ECG) waveform on a monitor. If the caregiver decides that it is appropriate, a defibrillation shock is administered. In many instances, this therapy is ineffective, although no known tool is available to predict a priori when defibrillation will be successful.

It has long been recognized that the efficacy of electrical defibrillation decreases with increasing duration of ischemia. See Eisenberg, M., et al., Paramedic programs and out-of-hospital cardiac arrest: I. Factors associated with successful resuscitation, *American Journal of Public Health*, 1979, vol. 69, pp. 30–38; Eisenberg, M., et al., Treatment of out-of-hospital cardiac arrest with rapid defibrillation by emergency medical technicians, *New England Journal of Medicine*, 1980, vol. 302, pp. 1379–83; and Roth, R., et al., Out-of-hospital cardiac arrest: factors associated with survival, *Annals of Emergency Medicine*, 1984, vol. 13, pp. 237–43.

It is known that decreasing the delay to defibrillation by introduction of automatic external defibrillators (AEDs) or other modifications improves survival from cardiac arrest in certain subsets of patients. See Auble, T., et al., Effect of out-of-hospital defibrillation by basic life support providers on cardiac arrest mortality: a metaanalysis, *Annals of Emergency Medicine*, 1995, vol. 25, pp. 642–47; and Stiell, I., et al., Improved out-of-hospital cardiac arrest survival through the inexpensive optimization of an existing defibrillation program: OPALS study phase II, *JAMA*, 1999, vol. 281, pp. 1175–81.

However, overall recovery from cardiac arrest outside the hospital remains low, perhaps because many applications of AEDs still occur beyond the time during which defibrillation is likely to be successful. Investigators have suggested that a brief period of artificial circulation or other tailored therapy could improve outcome for selected patients in whom defibrillation is unlikely to succeed. However, identification of these subsets of patients remains problematic. See Cobb, L., et al., Influence of cardiopulmonary resuscitation prior to defibrillation in patients with out-of-hospital ventricular fibrillation, *JAMA*, 1999, vol. 281, pp. 1182–88.

It is also known to employ quantitative measures of the VF waveform morphology to estimate the duration of VF and its likelihood of successful defibrillation. Callaham, M., et al., *Annals of Emergency Medicine*, 1993, vol. 22, pp. 1664–77; Weaver, W., et al., *Annals of Internal Medicine*, 1985, vol. 102, pp. 53–55; Brown, C., et al., *Annals of Emergency Medicine*, 1996, vol. 27, pp. 184–88; and Strohmenger, H., et al., *Anesthesia Analgesia*, 1994, vol. 79, pp. 434–38.

The only known prior quantitative descriptor of the ECG waveform during VF to gain widespread attention was centroid frequency—a measure derived from fast Fourier transforms. For example, a frequency measure based upon spectral analysis, the centroid frequency, varies with the duration of VF. Brown, C., et al., *Annals of Emergency Medicine*, 1989, vol. 18, pp. 1181–85. This measure has biphasic variation across time, preventing any single value of centroid frequency from predicting a unique state of the VF waveform. Because of the multiphasic profile, a particular value of the centroid frequency is not uniquely associated with a particular duration of VF.

VF is not completely random, but exhibits some deterministic organization. As shown in FIG. 1, early in VF, much of the power is concentrated in a narrow frequency band. Often there is a single peak in the spectral array representing a "dominant frequency." Alternatively, the center of mass of the entire curve can be calculated as the "centroid frequency" or "median frequency." Brown, C., et al., *Annals of Emergency Medicine*, 1989, vol. 18, pp. 1181–85. These measures change across time in a predictable fashion.

As shown in FIG. 2, centroid frequency (±SD) follows a predictable pattern after induction of VF in swine. Brown, C., et al., "Estimating the duration of ventricular fibrillation," *Annals of Emergency Medicine*, 1989, vol. 18, pp. 1181–85; Martin, D., et al., "Frequency analysis of the human and swine electrocardiogram during ventricular fibrillation," *Resuscitation*, 1991, vol. 22, pp. 85–91. This is, however, problematic since a given absolute value can occur at different times and the variance is substantial.

As shown in FIG. 3, in human VF, recorded from patients who developed VF while on Holter monitors, the initial peak of power in a narrow frequency range degenerates into a broad distribution of power among frequencies.

Unlike swine, as shown in FIG. 4, mean (±SD) centroid frequency from humans who developed VF while on Holter monitors has a less consistent change across time. Also, the absolute values of this measure differ between species. Martin, D., et al., *Resuscitation*, 1991, vol. 22, pp. 85–91. FIG. 4 shows a horizontal line indicating the number of subjects upon which the average and SD are based. The first 3 minutes of data includes 7 subjects, the next 2 minutes includes only 6 of those subjects, then 5, then 4.

Other studies have found that the amplitude of the VF waveform can predict defibrillation success. Callaham, M., et al., *Annals of Emergency Medicine*, 1993, vol. 22, pp. 1664–77; Weaver, W., et al., Annals of Internal Medicine, 1985, vol. 102, pp. 53–55. However, electrode configuration, placement, body habitus, impedance and recording equipment can affect amplitude measurements.

The waveform of VF is one possible predictor for the likelihood of successful defibrillation. VF waveform analysis is motivated by the obvious visual differences between a high-amplitude, lower frequency waveform seen in early VF and a low-amplitude, higher frequency waveform seen in later VF. However, both amplitude and frequency measures are difficult to apply in practice. See Callaham, M., et al., Prehospital cardiac arrest treated by urban first-responders: profile of patient response and prediction of outcome by ventricular fibrillation waveform, *Annals of Emergency Medicine*, 1993, vol. 22, pp. 1664–77 (amplitude measures); Weaver, W., et al., Amplitude of ventricular fibrillation waveform and outcome after cardiac arrest, *Annals of Internal Medicine*, 1985, vol. 102, pp. 53–55 (amplitude measures); Brown, C., et al., Signal analysis of the human ECG during ventricular fibrillation: frequency and amplitude parameters as predictors of successful countershock, *Annals of Emergency Medicine*, 1996, vol. 27, pp. 184–88 (frequency measures); and Strohmenger, H., et al., Frequency of ventricular fibrillation as a predictor of defibrillation success during cardiac surgery, *Anesthesia Analgesia*, 1994, vol. 79, pp. 434–38 (frequency measures).

For example, the amplitude is dependent upon recording conditions and equipment, while frequency measures can have identical values both early and late during VF. Brown, C., et al., Estimating the duration of ventricular fibrillation, *Annals of Emergency Medicine*, 1989, vol. 18, pp. 1181–85.

Significant improvements are needed for treatment of out-of-hospital cardiac arrest (OOHCA). In one series, defibrillation attempts failed to terminate VF or resulted in asystole 75% of the time. Hargarten, K., et al., Prehospital experience with defibrillation of coarse ventricular fibrillation: a ten-year review, *Annals of Emergency Medicine*, 1990, vol. 19, pp. 157–62.

It is well known from previous studies that repeated unsuccessful defibrillation attempts can increase myocardial damage and dysfinction, Gaba, D., et al. Internal countershock produces myocardial damage and lactate production without myocardial ischemia in anesthetized dogs, *Anesthesiology*, 1987, vol. 66, pp. 477–82; Ehsani, A., et al., Effects of electrical countershock on serum creatine phosphokinase (CPK) isoenzyme activity, *American Journal of Cardiology*, 1976, vol. 37, pp. 12–18, as well as increase the energy required for subsequent defibrillation, Bardy, G., et al., Prospective evaluation of initially ineffective defibrillation pulses on defibrillation success during ventricular fibrillation in survivors of cardiac arrest, *American Journal of Cardiology*, 1988, vol. 62, pp. 718–22. Furthermore, post-shock ECG changes indicative of myocardial damage increase with increasing energy delivered, and is believed to increase with multiple defibrillation attempts. Bardy, G., et al., Arrhythmias/pacing/heart block: multicenter comparison of truncated biphasic shocks and standard damped sine wave monophasic shocks for transthoracic ventricular defibrillation, *Circulation*, 1996, vol. 94, pp. 2507–14. This emphasizes the need to improve the likelihood of successful defibrillation by the first delivered shock in OOHCA.

While decreasing the interval from collapse to defibrillation is one approach for increasing resuscitation success, Stiell, I., et al., *JAMA*, 1999, vol. 281, pp. 1175–81, alternative strategies may improve outcomes for the remainder of patients with prolonged VF. Studies in animals have provided evidence that reperfusion (e.g., repeatedly forcing oxygenated blood through the heart by way of the blood vessels) and reoxygenation of the fibrillating heart can increase the probability of achieving an organized electrical activity after defibrillation. Niemann, J., et al., *Circulation*, 1992, vol. 85, pp. 281–287; Barton, C., et al., *Annals of Emergency Medicine*, 1996, vol. 27, pp. 610–616; and Strohmenger, H., et al., Resuscitation 1996;31:65–73. Likewise, the introduction of a 90-s period of cardiopulmonary resuscitation (CPR) prior to attempting defibrillation is noted to improve survival in humans. Cobb, L., et al., *JAMA*, 1999, vol. 281, pp. 1182–88. This beneficial effect of CPR prior to defibrillation is noted to affect predominantly those cases where the delay prior to arrival of therapy exceeded four minutes.

U.S. Pat. No. 5,676,690 discloses an implantable medical apparatus including a therapy unit, which produces a medical therapy regime that is administered by the apparatus to a subject. The apparatus obtains an electrical signal representing physiological activity of the subject and performs detrended fluctuation analysis on that signal in order to obtain a self-similarity parameter therefor. This analysis focuses on changes in the rate of an organized rhythm by looking at variability in the intervals between heartbeats. The self-similarity parameter or index can be made extra-corporeally available for use by a physician to evaluate the effectiveness of the current treatment program and/or can be employed by a control unit of the apparatus to automatically adjust the therapy regime (i.e., adjusting pacemaker settings in order to avoid dysythmias). For example, if the index for a patient in whom a pacemaker is implanted indicates that the patient is becoming seriously at risk of experiencing fibrillation (e.g., an index approaching 1.3 for ischemia), the physician may decide that implantation of a cardioverter or defibrillator is advisable, or perhaps that the patient should be placed on a pharmacological regimen in an effort to bring the patient's index back closer to the nominal value of 1.0 (healthy sinus rhythm). If a pharmacological regimen is prescribed, periodic monitoring of the index can then be used as an indicator of the effectiveness of the regimen.

U.S. Pat. No. 4,114,628 discloses a pacemaker that is capable of entering a defibrillating mode in which a one shot defibrillation pulse is automatically applied in the event of a heart stoppage for a prolonged period of time (e.g., 8 seconds). The pacemaker employs a defibrillating circuit which, in response to a predetermined number of inadequate responses to stimulating pulses, produces an output pulse to a counter to advance it to a maximum count. Then, after a defibrillating pulse, the counter automatically returns to its lowest count.

The prior art shows that there is room for improvement in the known methods and apparatus for defibrillation.

SUMMARY OF THE INVENTION

In contrast to amplitude and frequency measures, the fractal self-similarity dimension is a measure derived from nonlinear dynamics and fractal geometry for the analysis of the electrocardiogram (ECG) waveform during resuscitation from cardiac arrest. This provides a quantitative description of ventricular fibrillation (VF) waveform morphology. A simple, straight-line waveform will have a fractal dimension approaching one, whereas complex space-filling waveforms will have fractal dimensions approaching two. The fractal dimension is independent of signal amplitude and increases with duration of VF.

The present invention quantifies the character of the ECG waveform during VF in order to predict the response to therapy. In instances with a low likelihood of defibrillation success, other interventions, such as drug administration or chest compressions, might be attempted first.

Defibrillator shocks often fail to terminate VF in out-of-hospital cardiac arrest (OOHCA), and repeated failed shocks can worsen the subsequent response to therapy. Because the VF waveform changes with increasing duration of VF, it is possible that ECG analyses could estimate the pre-shock likelihood of defibrillation success. This method shows that an amplitude-independent measure of pre-shock VF waveform morphology predicts outcome after defibrillation.

The VF waveform in OOHCA can be quantified using the scaling exponent, and the value of the scaling exponent can predict the probability of successful defibrillation and survival to hospital discharge.

As one aspect of the invention, a defibrillator for selectively delivering a defibrillation pulse to a patient comprises: electrodes adapted for placement on the patient; a monitoring circuit for providing an electrocardiogram (ECG) of the patient; a defibrillation pulse generator including an energy store for delivering a defibrillation pulse; a switch in electrical communication with the monitoring circuit and the defibrillation pulse generator for selectively electrically connecting the monitoring circuit and the defibrillation pulse generator to the electrodes; and a control system in electrical communication with the monitoring circuit, the defibrillation pulse generator, and the switch for: (i) causing the switch to electrically connect the monitoring circuit to the electrodes in order to provide the ECG of the patient, (ii) determining a scaling exponent for the patient from the ECG thereof, and (iii) comparing the scaling exponent to a predetermined value and selectively causing the switch to electrically connect the defibrillation pulse generator to the electrodes in order that the energy store delivers the defibrillation pulse to the patient.

As another aspect of the invention, a method of selectively delivering a defibrillation pulse to a patient comprises the steps of: placing electrodes on the patient; taking an electrocardiogram (ECG) of the patient; determining a scaling exponent for the patient from the ECG thereof; comparing the scaling exponent to a predetermined value; and selectively delivering a defibrillation pulse through the electrodes to the patient based upon the comparing step.

Preferably, the method comprises selectively displaying a suggested alternative therapy for the patient when the scaling exponent is greater than the predetermined value. Suggested alternative therapies may include: employing reperfusion; reoxygenating a fibrillating heart of the patient, and employing defibrillation after the reoxygenating step; employing a period of cardiopulmonary resuscitation (CPR); employing artificial perfusion, and employing defibrillation after the employing artificial perfusion step; or employing at least one of cardiopulmonary resuscitation (CPR) and ventilating the patient.

Preferably, the defibrillation pulse is selectively delivered to the patient when the scaling exponent is less than the predetermined value. A suggested alternative therapy may be displayed when the scaling exponent is greater than the predetermined value.

As a preferred refinement, the steps of taking an ECG, determining a scaling exponent, comparing the scaling exponent, and selectively delivering a defibrillation pulse are employed in real time.

As a further aspect of the invention, a defibrillator for selectively delivering a defibrillation pulse to a patient comprises: electrodes adapted for placement on the patient; a monitoring circuit for providing an electrocardiogram (ECG) of the patient; a defibrillation pulse generator including an energy store for delivering a defibrillation pulse; a switch in electrical communication with the monitoring circuit and the defibrillation pulse generator for selectively electrically connecting the monitoring circuit and the defibrillation pulse generator to the electrodes; and a control system in electrical communication with the monitoring circuit, the defibrillation pulse generator, and the switch for: (i) causing the switch to electrically connect the monitoring circuit to the electrodes in order to take the ECG of the patient, (ii) determining a scaling exponent for the patient from the ECG thereof, (iii) displaying the scaling exponent, and (iv) receiving an input responsive to the displaying and selectively causing the switch to electrically connect the defibrillation pulse generator to the electrodes in order that the energy store delivers the defibrillation pulse to the patient.

As a still further aspect of the invention, a method of diagnosing and treating a patient comprises the steps of: placing electrodes on the patient; taking an electrocardiogram (ECG) of the patient; determining a scaling exponent for the patient from the ECG thereof; displaying the scaling exponent; receiving an input responsive to the step of displaying the scaling exponent; and selectively defibrillating the patient responsive to the receiving step.

Preferably, an input from an operator is employed as the input responsive to the step of displaying the scaling exponent.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

As employed herein, the term "patient" shall mean human beings and other members of the animal kingdom.

Figure 1:
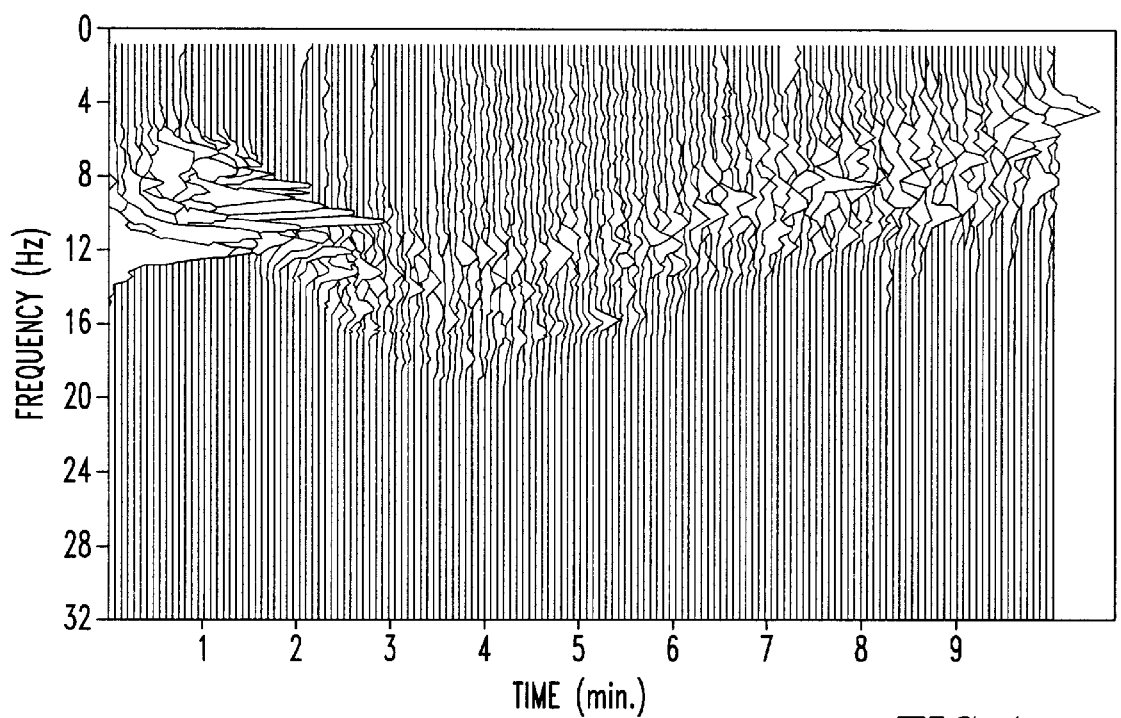
FIG. 1 is a plot of frequency versus time for human ventricular fibrillation (VF).
Figure 2:
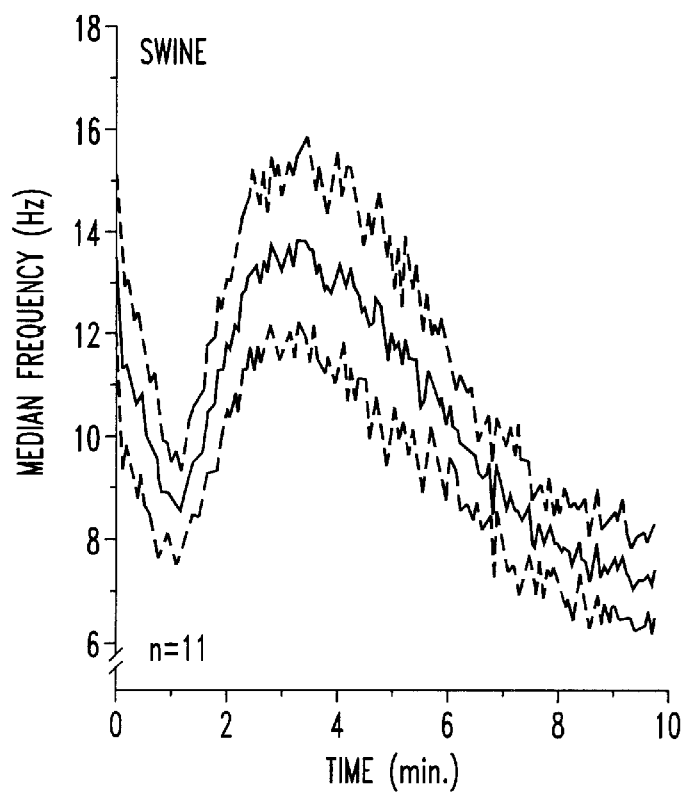
FIG. 2 is a plot of centroid (median) frequency (±SD) versus time after induction of VF in swine.
Figure 3:
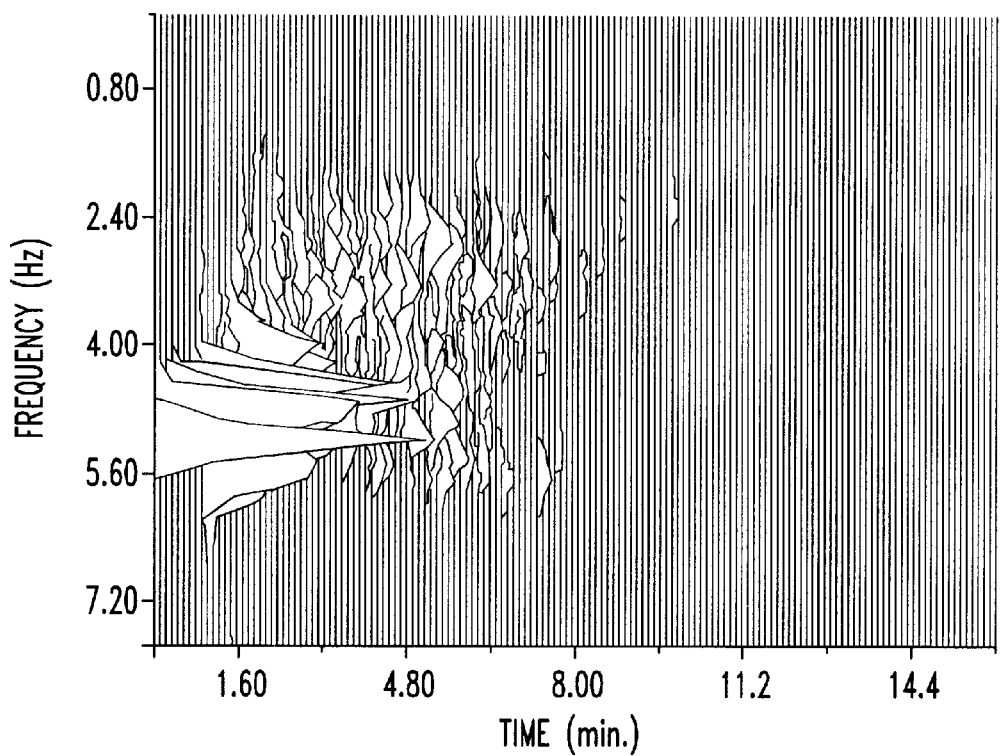
FIG. 3 is a plot of frequency versus time for human VF, recorded from patients who developed VF while on Holter monitors.
Figure 4:
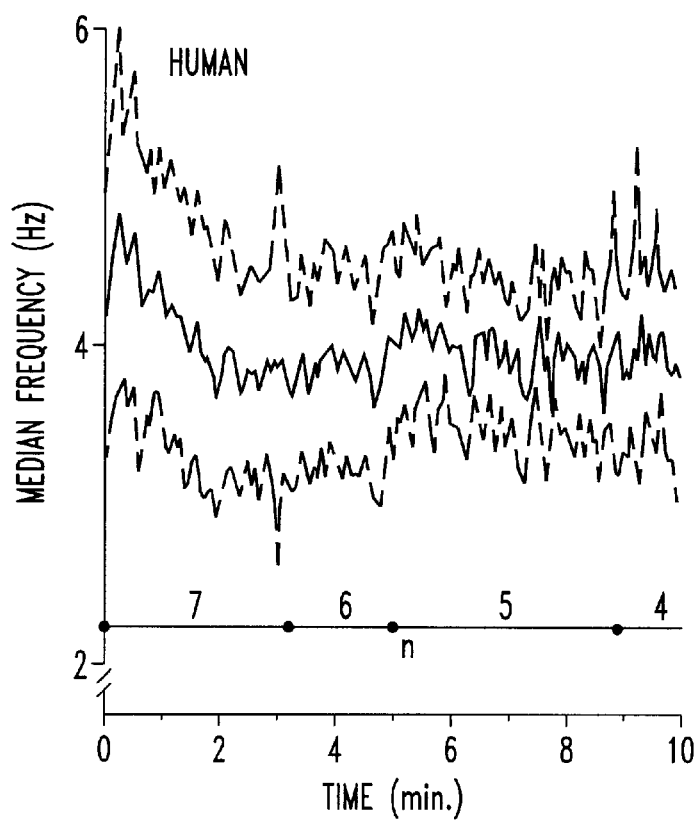
FIG. 4 is a plot of centroid (median) frequency (±SD) versus time, recorded from humans who developed VF while on Holter monitors.
Figure 5:
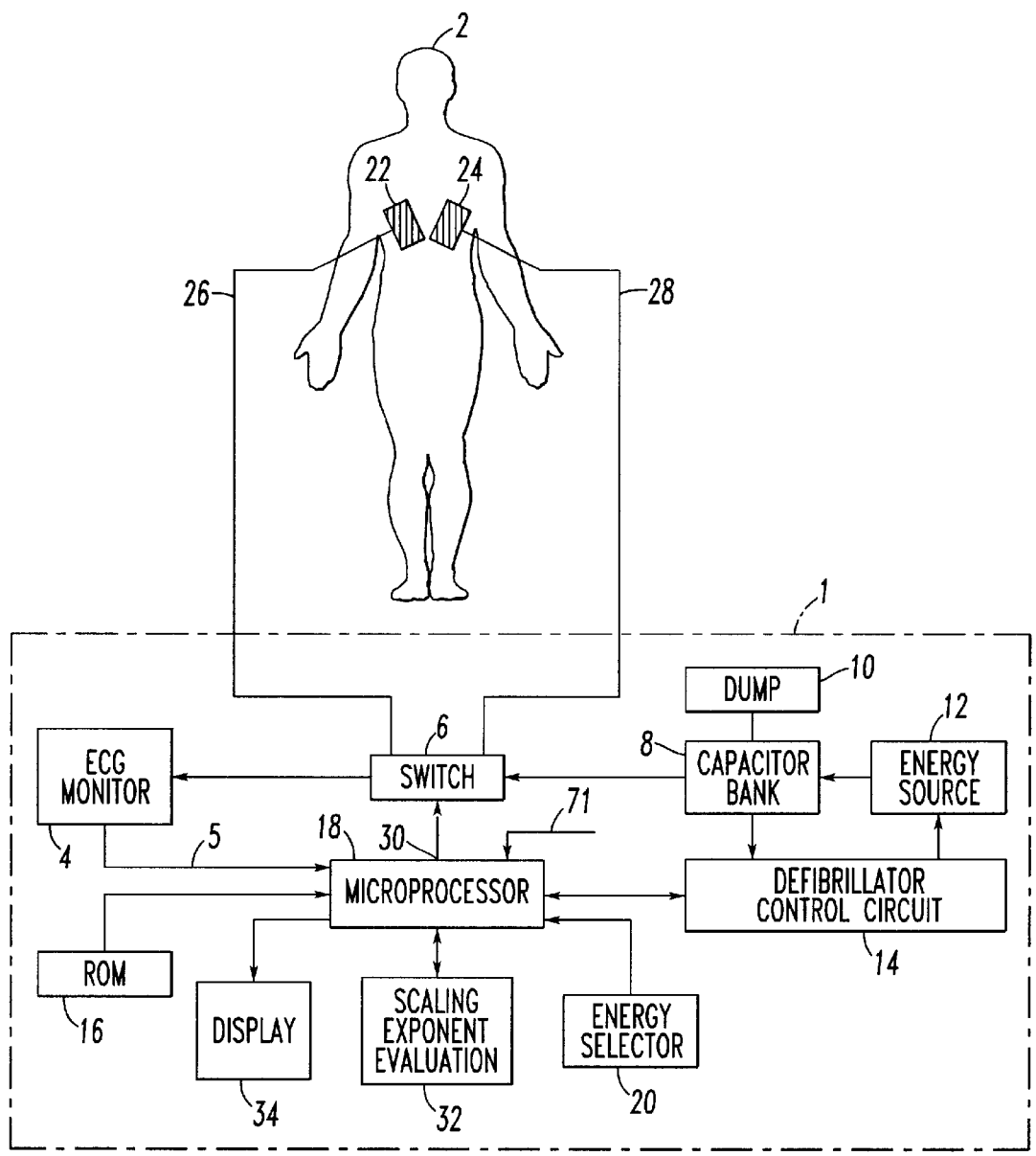
FIG. 5 is a block diagram of a defibrillator formed in accordance with the present invention and electrically connected to a patient for defibrillation.

Referring to FIG. 5, an exemplary defibrillator 1 for selectively delivering a defibrillation pulse to a patient 2 is illustrated. The defibrillator 1 includes an electrocardiogram (ECG) monitoring circuit 4 for taking an ECG 5 of the patient 2, a switch 6, an energy store such as the exemplary capacitor bank 8, an energy dump 10, an energy source 12, a defibrillator control circuit 14, a memory such as the exemplary read only memory (ROM) 16, a microprocessor 18, an energy selector 20, and patient electrodes 22,24 adapted for placement on the patient 2.

The switch 6 is in electrical communication with the monitoring circuit 4 and the capacitor bank 8 for selectively electrically connecting the monitoring circuit 4 and the capacitor bank 8 to the electrodes 22,24, which are electrically connected to the switch 6 via respective conductors 26,28. The microprocessor 18 is in electrical communication with the monitoring circuit 4, the defibrillator control circuit 14, and the switch 6. The microprocessor 18 has an output 30 having a first state that causes the switch 6 to electrically connect the monitoring circuit 4 to the electrodes 22,24 in order to provide the ECG 5 of the patient 2. The output 30 also has a second state that causes the switch 6 to electrically connect the capacitor bank 8 to the electrodes 22,24 in order to deliver the defibrillation pulse to the patient 2.

According to one aspect of the invention, the defibrillator 1 calculates a scaling exponent for the patient 2 before determining whether or not to deliver a defibrillation pulse. As discussed in greater detail below in connection with FIGS. 6A–6D and 7A, the microprocessor 18 includes a scaling exponent evaluation routine 32 that determines the scaling exponent for the patient 2 from the ECG 5, compares the scaling exponent to a predetermined value and, based upon the comparison, selectively causes the switch 6 (via the second state of the output 30) to electrically connect the capacitor bank 8 to the electrodes 22,24 and, thus, deliver the defibrillation pulse.

The exemplary defibrillator 1 also includes a display 34 operatively associated with the microprocessor 18 for displaying the scaling exponent, and a non-volatile memory, such as the exemplary ROM 16, for storing control programs and the predetermined value employed by the routine 32. A suitable display, such as the exemplary liquid crystal display (LCD) 34, allows one or more ECG channels to be viewed simultaneously, with up to about 8 seconds of cascading ECG, although certain embodiments of the invention may be implemented on a defibrillator which does not employ a display.

Preferably, the microprocessor 18 employs a suitable analysis program (not shown) to offer interpretive ECG analysis. For example, such a program simultaneously acquires, analyzes and records a plurality of ECG channels on a printer (not shown) in the standard format.

The patient electrodes 22,24 may, for example, can be hand-held electrode paddles or adhesive electrode pads placed on the skin of a patient. The patient's body provides an electrical path between these electrodes. When using hand-held electrode paddles, the defibrillator 1 preferably prompts the operator to hold and retain the paddles firmly on the patient's thorax throughout the ECG monitoring, scaling exponent calculation, and defibrillation procedure of the present invention.

The energy selector 20 supplies energy setting information to the microprocessor 18 and instructs the defibrillator 1 regarding the defibrillation pulse energy to be delivered to a patient 2. While the energy selector 20 may be in the form of a continuous dial, in a preferred embodiment, the energy selector 20 permits selection of a suitable energy level from a set number of discrete energy levels, such as 100 joules, 200 joules, 300 joules, and 360 joules, for example. If desired, such as in the case of an automated external defibrillator with preprogrammed energy levels, the energy selector 20 may be eliminated.

The switch 6 couples the electrodes 22,24 to either the input of the monitoring circuit 4 or to the output of the capacitor bank 8, based on the state of the control signal received from the output 30 of the microprocessor 18. The switch 6 is of conventional design and may be formed of electrically operated relays. Alternatively, an arrangement of suitable solid state devices, such as silicon controlled rectifiers or insulated gate bipolar transistors, may be employed.

An example of a defibrillator, but excluding the exemplary scaling exponent evaluation routine 32, scaling exponent display 34 and non-volatile memory for the predetermined value disclosed herein, is a LIFEPAK 12 defibrillator/monitor marketed by Medtronic Physio-Control Inc. of Redmond, Wash. Such defibrillator/monitor provides therapeutic and diagnostic functions in a single relatively small device designed for both out-of-hospital and hospital users, and provides the flexibility to add new features and enhancements at a future date. In an automatic defibrillation mode, a shock advisory system advises the operator when it detects a shockable rhythm. For example, when analysis of the ECG is consistent with VF, the machine can provide an audible (and/or visual) alert that "Shock is advised"; whereas when analysis of the ECG is consistent with an organized rhythm such as normal sinus rhythm the machine can provide an audible (and/or visual) alert to "Check pulses."

In a manual defibrillation mode, the defibrillator/monitor operates without this advisory function. Preferably, the exemplary scaling exponent evaluation routine 32 may be integrated within the automatic defibrillation mode. By determining the scaling exponent within the automatic mode, the defibrillator/monitor may provide more detailed instructions. For example, when analysis of the ECG is consistent with VF, and the scaling exponent is less than a threshold value, such as 1.3, the defibrillator/monitor may provide an exemplary audible (and/or visual) alert that "Shock is advised;" whereas when analysis of the ECG is consistent with VF, and the scaling exponent is greater than the threshold, the defibrillator/monitor may provide an exemplary audible (and/or visual) alert that "Shock is unlikely to succeed" or "Perform further therapy prior to shock."

A suitable power adapter (not shown) provides line power as well as a battery charging capability to the defibrillator 1.

The ECG waveform during ventricular fibrillation (VF) has chaotic properties with positive Lyapunov exponents and defined embedding dimensions. The geometric structure of the VF waveform can be described quantitatively using several measures from fractal geometry. These measures include the fractal self-similarity dimension and Hurst exponents. Several different numerical techniques for estimating these measures provide similar values. The most robust and numerically simplest algorithm for estimating the fractal self-similarity dimension consists of calculating the "scaling exponent."

The scaling exponent is calculated from a digital sample of ECG by determining the sum of absolute changes in potential across the whole sample using various sampling rates. In turn, the rate with which the log of the sum of potential changes varies with the log of the sampling rate is calculated. This rate is an estimate of the fractal self-similarity dimension, and is linearly related to the Hurst exponent. This measure may be reliably calculated using a 5-s sample of ECG and is independent of the absolute amplitude of the recording. Plots of a graph of the log of the sum of potential changes versus the log of the sampling rate may be used to recognize the quality of the ECG data and to distinguish the aperiodic VF from cyclic noise and from other ECG rhythms.

Scaling exponents are calculated for an exemplary 5.12 s epoch (2048 samples) of the VF waveform that began 10 s prior to the first defibrillation attempt. This sampling point is selected as an interval free of artifact, during which the automatic external defibrillator (AED) is instructing the first responders to stand clear. The sample size of 5.12 s or 2048 points provides a reliable estimate of the scaling exponent. Preferably, the VF waveform sampling is at least about 200–300 samples per second, with about 400 samples per second being highly preferred.

The scaling exponent is a measure derived from fractal geometry that characterizes the "roughness" or "smoothness" of the ECG waveform. It is an estimate of the fractal self-similarity dimension. Higuchi, T., Approach to an irregular time series on the basis of the fractal theory, Physica D, 1988, vol. 31, pp. 277–83.

A 5.12 s epoch of the ECG waveform is expressed as a time series of M (e.g., M=2048) voltage measurements, X(1), X(2), X(3) ... X(i) ... The sum, L, of the absolute potential differences between each i-th measurement of the ECG waveform, X(i), and the measurement k points later, X(i+k), is calculated over the entire epoch. The separation or lag, k, is varied from 1 (differences between each measurement) to 2000 (differences between each 2000-th measurement). The sums for each value of k are normalized by a factor, [M/k(M-k)], to account for the different number of intervals sampled for different values of k within a finite epoch to describe a function L(k):

$$L(k) = M / (k(M-k)) \times \sum_{i=1}^{M-k} |X(i) - X(i+k)| \quad \text{(Eq. 1)}$$

The resulting values of L(k) may be fitted to an exponential function describing the scaling relationship between L(k) and the lag, k:

$$L(k) = k^{(1-d)} \quad \text{(Eq. 2)}$$

wherein:

d is the scaling exponent.

This function of Equation 2 describes a curve with a consistent plateau in the region centered between k=5 and k=20. In order to standardize the estimation of the scaling region, the inflection point of the log-log plot of L(k) versus k is determined by a PC-compatible computer by calculating the local slope of the curve for five point regions centered around each point and identifying the maximum. The slope of a least-squares line is fitted to the log-log plot of L(k) versus k using ten points centered around the inflection point. The scaling exponent d is calculated from Equation 3, as shown in FIGS. 6A–6B and 6C–6D:

$$d = 1 - \text{slope} \quad \text{(Eq. 3)}$$

Figure 6A:
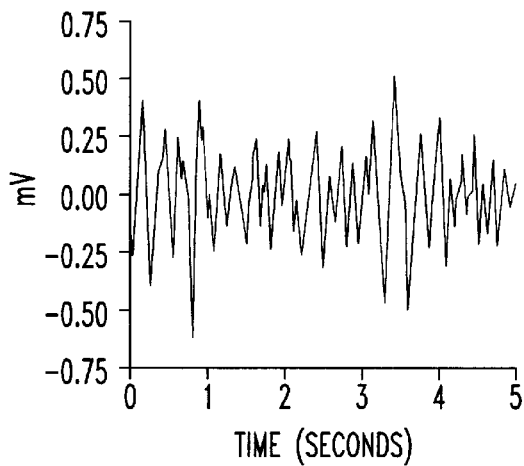
FIGS. 6A and 6C are plots of AED-recorded electrocardiograms (ECGs) from representative subjects with successful and failed defibrillation attempts, respectively.
Figure 6B:
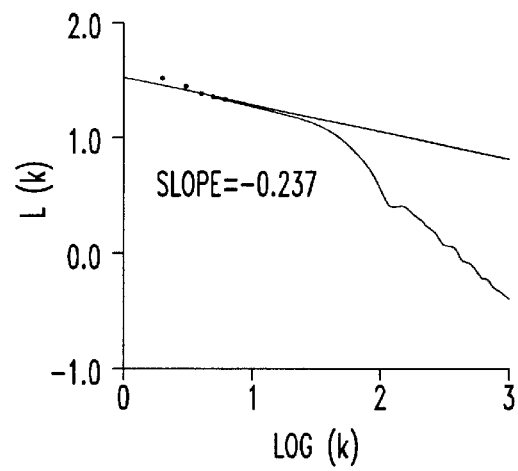
FIGS. 6B and 6D are log-log plots for the calculation of the scaling exponent as an estimate of the fractal self-similarity dimension for the plots of FIGS. 6A and 6C, respectively.
Figure 6C:
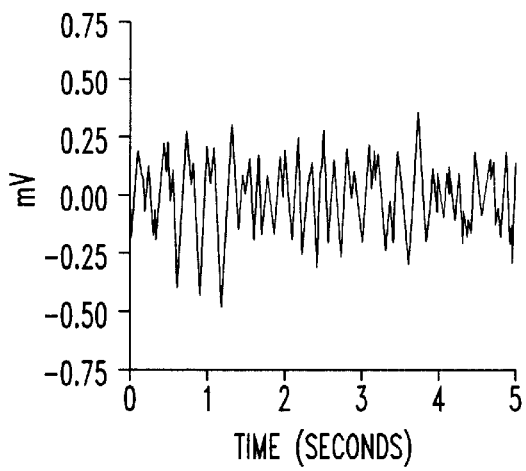
Figure 6D:
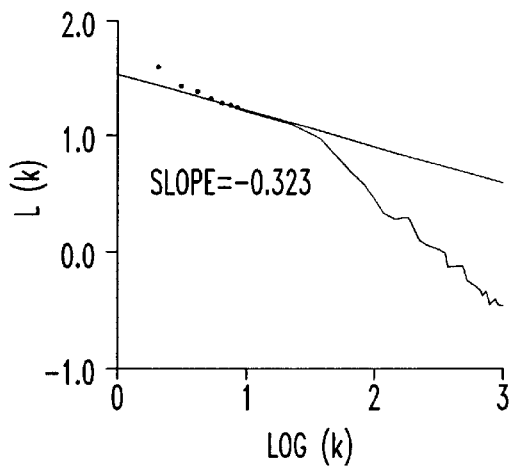

The sum of the absolute potential differences (L(k)) between sampling points of the VF waveform are plotted against the lag, k, on log-log axes (of FIGS. 6B and 6D). The slope of the resulting plot is calculated at the inflection point of this curve, and the scaling exponent is defined as "1-slope".

In the examples of FIGS. 6A–6D, successful defibrillation resulted for the case (FIGS. 6A and 6B) where the slope is −0.237 (i.e., the scaling exponent=1.237), whereas failed defibrillation resulted for the case (FIGS. 6C and 6D) where the slope is −0.323 (i.e., the scaling exponent=1.323).

EXAMPLE 1

An examination of whether the fractal dimension of the VF waveform recorded by AEDs predicts the success of defibrillation is undertaken in a series of patients suffering out-of-hospital cardiac arrest (OOHCA). In particular, the scaling exponent is calculated as a measure of the self-similarity dimension in the VF waveform. In turn, the ability of the scaling exponent to predict the success of defibrillation by the AED is assessed. As calculated, the scaling exponent is linearly related to the Hurst exponent, but is easier to calculate.

Details of AED application by police first-responders is disclosed in Davis, E., et al., Performance of police first responders in utilizing automated external defibrillation on victims of sudden cardiac arrest, *Prehospital Emergency Care,* 1998, vol. 2, pp. 101–07; Davis, E., et al., Institution of a police automated external defibrillation program: concepts and practice, *Prehospital Emergency Care,* 1999, vol. 3, pp. 60–65; and Mosesso, V., et al., Use of automated external defibrillators by police officers for treatment of out-of-hospital cardiac arrest, *Annals of Emergency Medicine,* 1998, vol. 32, pp. 200–07.

Because the likelihood of successful defibrillation decreases over time and the scaling dimension increases over time, it is believed that a lower scaling dimension in the initial VF waveform is correlated with successful defibrillation.

EXAMPLE 2

Police in seven suburban municipalities in Allegheny County, Pennsylvania are provided with LIFEPAK 300 semiautomatic defibrillators marketed by Physio-Control. This region is a 46 square mile suburb of Pittsburgh with a total population of about 145,000. Emergency medical services in these communities are provided by three agencies with average annual emergency call volumes of 2700, 3500 and 4000. In each community, police are routinely dispatched to medical emergencies, and arrive prior to paramedics in about 50% of cases. Training of police first responders in the use of the AED consisted of an initial four-hour program based upon AHA guidelines, followed by quarterly review sessions. Data are collected from these police services. Training and data collection methods are disclosed in Davis, E., et al., Performance of police first responders in utilizing automated external defibrillation on victims of sudden cardiac arrest, *Prehospital Emergency Care*, 1998, vol. 2, pp. 101–07; Davis, E., et al., Institution of a police automated external defibrillation program: concepts and practice, *Prehospital Emergency Care*, 1999, vol. 3, pp. 60–65; and Mosesso, V., et al., Use of automated external defibrillators by police officers for treatment of out-of-hospital cardiac arrest, *Annals of Emergency Medicine*, 1998, vol. 32, pp. 200–07.

The subjects for this study are adult patients (18 years or older) with nontraumatic cardiac arrest for whom an initial rhythm of VF is recorded by the AED. For each patient, the recording leads / defibrillation pads (e.g., FAST-PATCH marketed by Physio-Control) of the AED are applied to the chest. The ECG waveform is recorded on analog tapes along with an audio record. After each AED use, these tapes are collected by the investigators along with clinical information about each patient. Audio and ECG recordings are only available for a subset of the patients treated by police first responders. All subjects for whom ECG recordings could be obtained are included.

Analysis of the ECG recording from each AED is conducted off-line. The ECG waveform is digitized at 400 samples/second from the analog tape recordings using a PC-compatible computer and an analog/digital converter PowerLab, marketed by AD Instruments, of Castle Hill, Australia. The resulting digital records are analyzed using a Chart software package, also marketed by AD Instruments, as well as suitable application software written in C. After selecting the epoch, all calculations are performed entirely by the PC-compatible computer.

EXAMPLE 3

The scaling exponent is compared between cases with successful or failed defibrillations. Successful defibrillations are defined as cases in which the shock resulted in an organized rhythm on ECG that is sustained for at least 30 s with or without a pulse. Failed defibrillations either resulted in continued VF or asystole (unorganized rhythms). Although asystole is often considered a successful defibrillation from an electrophysiological standpoint, Poole, J., et al., Low-Energy impedance-compensating biphasic waveforms terminate ventricular fibrillation at high rates in victims of out-of-hospital cardiac arrest, *Journal of Cardiovascular Electrophysiology*, 1997, vol. 8, pp. 1373–85, defining success based upon the dichotomy between organized and unorganized post-shock rhythms is believed to be more relevant to clinical outcome, Niemann, J., et al., Treatment of prolonged ventricular fibrillation. Immediate countershock versus high-dose epinephrine and CPR preceding countershock, *Circulation*, 1992, vol. 85, pp. 281–87. Preliminary analyses also indicate that the scaling measures do not distinguish between subjects with post-shock asystole and subjects with persistent VF.

Figure 7A:
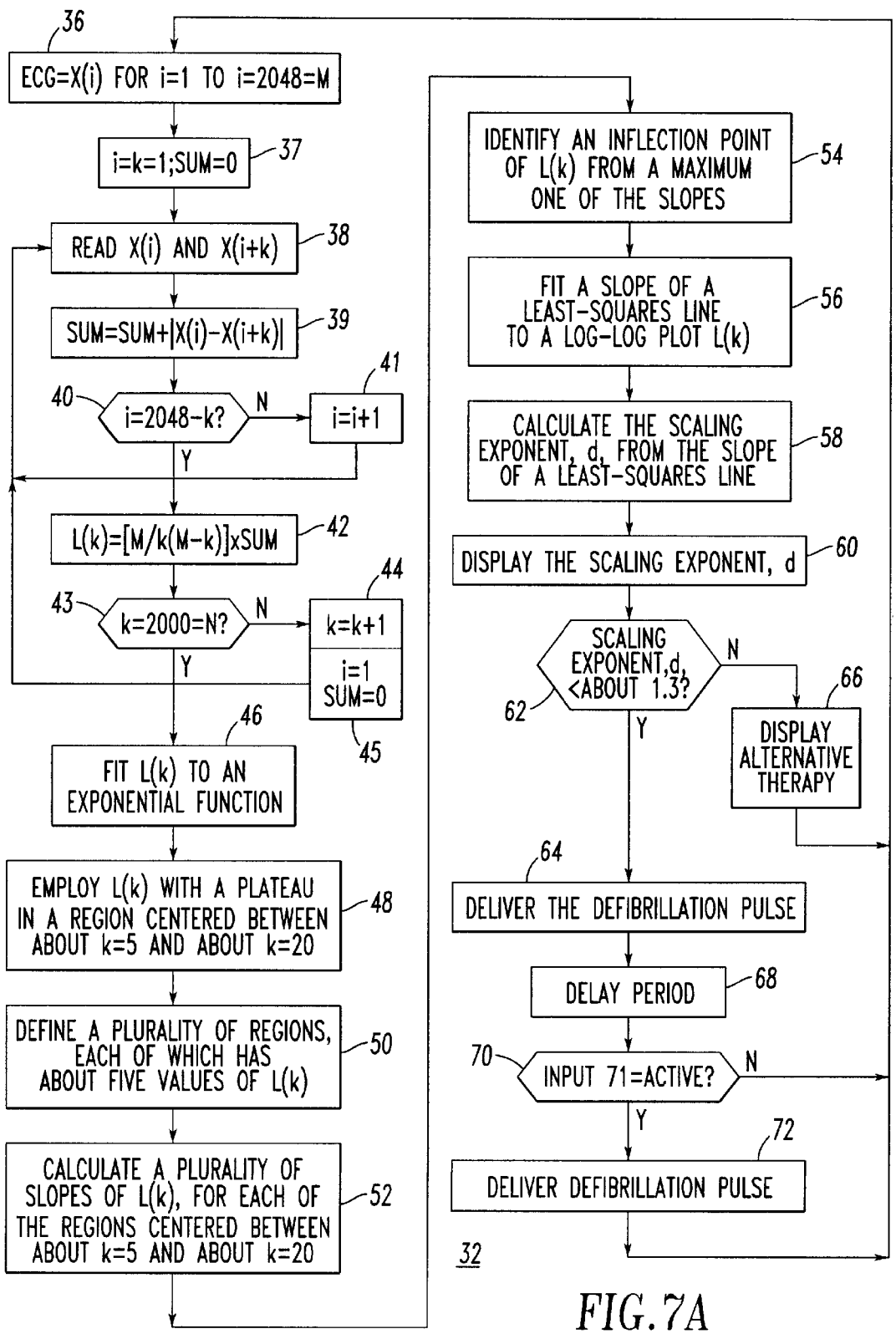
FIGS. 7A and 7B are flowcharts of scaling exponent evaluation routines in accordance with the present invention.

Referring to FIG. 7A, a flowchart of the scaling exponent evaluation routine 32 is illustrated. First, at 36, the ECG 5 of FIG. 5 is expressed as series of a plurality of voltage measurements, X(i) for i=1 to i=2048=M. Next, at 37, the index variable, i, and the lag, k, are both set to 1, and a variable, SUM, is set to 0. The lag of 1 means that a difference will be calculated between adjacent pairs of the voltage measurements.

Next, at 38–46 and 48–58 (even reference numbers), the scaling exponent is calculated. Steps 38–45 calculate Equation 1 for all values of the lag, k. First, at 38, two voltages measurements X(i) and X(i+k) are read from the ECG 5. At 39, the variable SUM is increased by the absolute value of the difference between the two voltage measurements X(i) and X(i+k). At 40, if the index variable, i, is not equal to the limit, 2048-k, then, at 41, the index is incremented before repeating step 38. Otherwise, at 42, employing M=2048 as a count of the voltage measurements, the variable SUM is multiplied by a normalizing factor, [M/k(M−k)].

Next, at 43, if the lag, k, is equal to the limit, N=2000 (i.e., a difference between each 2000th pair of the voltage measurements), then, at 44, the lag is incremented, and, at 45, the index variable, i, is set to 1, and the variable, SUM, is set to 0, before step 38 is repeated. Otherwise, if all 2000 values of L(k) have been calculated, then, at 46, values of the function, L(k), are fitted to the exponential function of Equation 2 in order to describe a scaling relationship between the function, L(k), and the lag, k, according to the scaling exponent, d.

At 48, the function, L(k), is employed with a plateau in a region centered between about k=5 and about k=20. A plurality of regions are defined, at 50, each of which has about five values of the function, L(k). Then, at 52, a plurality of slopes of the function, L(k), are calculated for each of the regions centered between about k=5 and about k=20. At 54, an inflection point of the function, L(k), is identified from a maximum one of the slopes. Then, at 56, a plurality of points centered around the inflection point are employed and a slope of a least-squares line is fitted to a log-log plot of the function, L(k). Next, at 58, the scaling exponent, d, is calculated from the slope of the least-squares line. The scaling exponent, d, is preferably displayed at 60.

At 62, if the scaling exponent, d, is less than the predetermined value (e.g., about 1.3), then the defibrillation pulse is selectively delivered, at 64, to the patient 2. On the other hand, if the scaling exponent, d, is greater than the predetermined value (e.g., about 1.3), then, at 66, a suggested alternative therapy for the patient 2 is alternatively selectively displayed on the display 34 of FIG. 5.

For example, the suggested alternative therapy may be selected from the list comprising: (1) reperfusion; (2) reoxygenating the fibrillating heart of the patient; and then employing defibrillation; (3) employing a period of cardiopulmonary resuscitation (CPR), and then defibrillation; (4) employing artificial perfusion, and then employing defibrillation; and (5) employing one or both of CPR and ventilating the patient, and then employing defibrillation.

Preferably, the steps 36 (i.e., taking the ECG), 37–46 and 48–58 (even reference numbers) (i.e., calculating the scaling exponent), 62 (i.e., comparing the scaling exponent), and 64 (i.e., selectively delivering the defibrillation pulse) are performed in real time. Finally, after a suitable delay period 68 (e.g., to allow input amplifiers to stabilize), the routine 32 may be repeated in order to permit the operator the deliver another defibrillation pulse. At 70, a microprocessor input 71 is tested to determine if a manual override of the steps 36–46 and 48–68 (even reference numbers) is requested. If not, then execution resumes at step 36. Otherwise, at 72, a manually initiated defibrillation pulse is initiated.

Although an exemplary routine 32 has been described for calculating the scaling exponent, a wide range of variations are possible. For example, the scaling exponent may be continuously calculated by performing steps 36, 37–46 and 48–60 (even numbers) by using the last 2048 ECG points sampled. The last 5.12 seconds of ECG may be held in a buffer X(1) ... X(i) ... X(2048), that is continuously updated every 0.0025 seconds by replacing X(i) with X(i+1) and by replacing X(2048) with the current voltage measured from the patient electrodes 22,24.

Figure 7B:
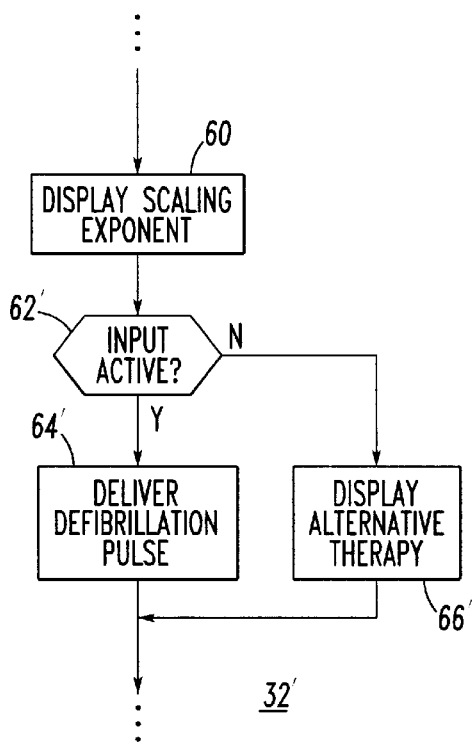

FIG. 7B illustrates a flowchart of an alternative scaling exponent evaluation routine 32'. The routine 32' is the same as the routine 32 of FIG. 7A, except that steps 62,64,66 are replaced by steps 62',64',66', respectively. For ease of illustration, only those latter steps and step 60 are shown in FIG. 7B. At 60, the scaling exponent, d, is displayed. Following a suitable delay for operator response, at 62', the input 71 of FIG. 5 is tested to see if it is active. In this manner, the operator may respond to the scaling exponent, d, as displayed at step 60. If so, then at 64', the defibrillation pulse is selectively delivered to the patient 2. On the other hand, if the input 71 is not active, then, at 66', a suggested alternative therapy for the patient 2 is alternatively selectively displayed on the display 34 of FIG. 5. Hence, steps 62' and 64' selectively cause the switch 6 to electrically connect the capacitor bank 8 to the electrodes 22,24 in order to deliver the defibrillation pulse to the patient 2.

Figure 7C:
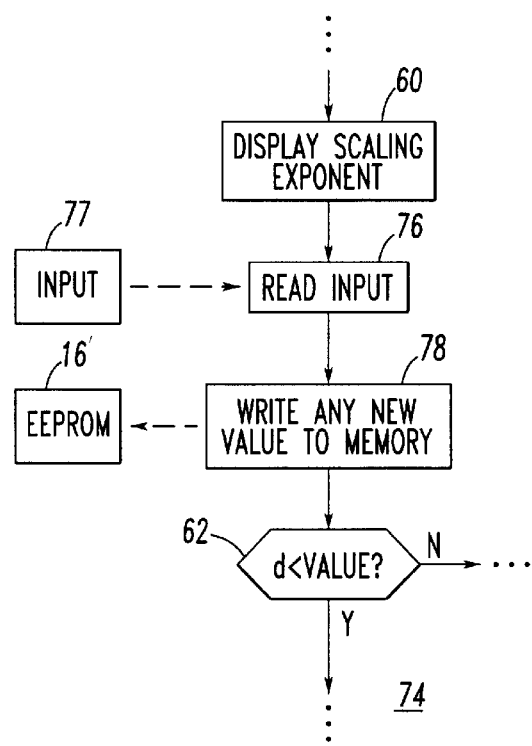
FIG. 7C is a flowchart of an alternative routine for entering or adjusting the predetermined value, which may be employed with the scaling exponent evaluation routine of FIG. 7A.

FIG. 7C is a flowchart of a routine 74 for entering or adjusting the predetermined value employed by the scaling exponent evaluation routine 32 of FIG. 7A. In this example, the microprocessor 18 of FIG. 5 employs a suitable non-volatile memory 16' (e.g., non-volatile RAM, EEPROM) which stores the predetermined value (e.g., which might be set to an initial exemplary predetermined value of 1.3). At 76, the microprocessor 18 reads an input 77 that may define a new value. Then, at 78, the microprocessor 18 writes any new value to the non-volatile memory 16'. Preferably, the routine 74 is incorporated prior to step 62 of FIG. 7A, in order to permit a newly entered or adjusted predetermined value to be incorporated prior to evaluating the scaling exponent and selectively delivering the defibrillation pulse. For example, future research (e.g., acquisition of larger data sets) might indicate that the predetermined value should be adjusted upward or downward (e.g., 1.29 or 1.31, respectively) as a threshold for likely successful defibrillation.

EXAMPLE 4

Data is also collected for cases about the return of a spontaneous circulation (ROSC) at any time during the resuscitation, survival to hospital admission, and survival to hospital discharge. Characteristics are compared between cases with successful and unsuccessful defibrillation using t-test for continuous variables and Chi-square for categorical variables. The mean scaling exponent is compared between cases with successful defibrillation and unsuccessful defibrillation using t-test. The proportions of subjects with good clinical outcomes are compared for different ranges of the scaling exponent using Chi-square. Relationships between continuous variables are examined with Pearson's product-moment correlation. A stepwise logistic regression is performed by employing SPSS-PC, marketed by SPSS Inc., of Chicago, Ill., to develop a model for predicting the probability of successful defibrillation. Defibrillation success is expressed as a binary variable. Predictor variables include age, sex, time from call received until defibrillation, absence or presence of bystander CPR, whether collapse is witnessed or unwitnessed, and value of the scaling exponent. At each step, the candidate predictor variable with the highest association with the dependent variable is introduced into the model, and variable entry is halted when the resulting improvement in the fit of the model is not significant. Identical logistic regression is performed to identify contributing variables that predict the likelihood of ROSC, admission to the hospital or discharge from the hospital. For all statistics, the criterion for significance is $p<0.05$.

EXAMPLE 5

AED recordings are obtained from 75 cases of cardiac arrest in which the presenting rhythm is VF, and in which police first responders attempted defibrillation prior to any other advanced life support. During the study interval, the community EMS systems responded to 649 cases of cardiac arrest, and VF is the initial rhythm in 222 cases. Police first responders applied an AED and attempted the initial defibrillation in 89 cases. The 75 cases employed for this analysis represent all cases for which ECG waveform recordings are successfully retrieved from the AED.

The first defibrillation by the AED is successful in converting VF into an organized electrical rhythm in 31 cases (41.3%). Successful defibrillation by the first AED shock is associated with ROSC during the resuscitation, as shown in Table 1 (Chi-Square=4.05, df=1, p=0.044).

TABLE 1

Characteristics of Study Population Response to First Defibrillation

|  | Organized Rhythm (Success) | VF or Asystole (Failure) |
|---|---|---|
| Number (N) | 31 | 44 |
| Age (years) | 60.6 ± 15.5 | 66.7 ± 12.0 |
| Sex (% male) | 74.2% | 75.0% |
| Witnessed (%) | 74.2% | 70.5% |
| Bystander CPR (%) | 45.2% | 34.1% |
| Call Received to Paramedic Arrival (minutes) | 6.0 ± 2.5 | 7.1 ± 2.9 |
| Call Received to Defibrillation (minutes) | 5.9 ± 1.9 | 6.7 ± 2.3 |
| ROSC (%) | 64.5% | 43.2% |
| Survival to Hospital Admission (%) | 41.4% | 23.1% |
| Survival to Hospital Discharge (%) | 29.0% | 9.1% |

Although more of the subjects with successful AED defibrillation are admitted to the hospital, this difference is not significant. The proportion of subjects discharged alive from the hospital is higher after successful AED defibrillation as shown in Table 1 (Chi-Square=5.05, df=1, p=0.025). Also, age, sex ratio, proportion where collapse is witnessed, proportion with bystander CPR, and delay from receiving call to delivery of defibrillation does not differ between groups with successful and failed defibrillation.

Analysis of the VF waveform confirms that a scaling relationship exists between the lag, k, and the sum of potential changes, L(k). The region of scaling is consistently observed for values of log(k) between 0.6 and 1.2, corresponding to sampling frequencies between 25 Hz and 100 Hz. The least-squares line fitted to the ten points centered on the inflection point of this scaling region has high correlation coefficients (i.e., range: 0.967–0.999). The value of the scaling exponent ranges from 1.11 to 2.00.

Figure 8:
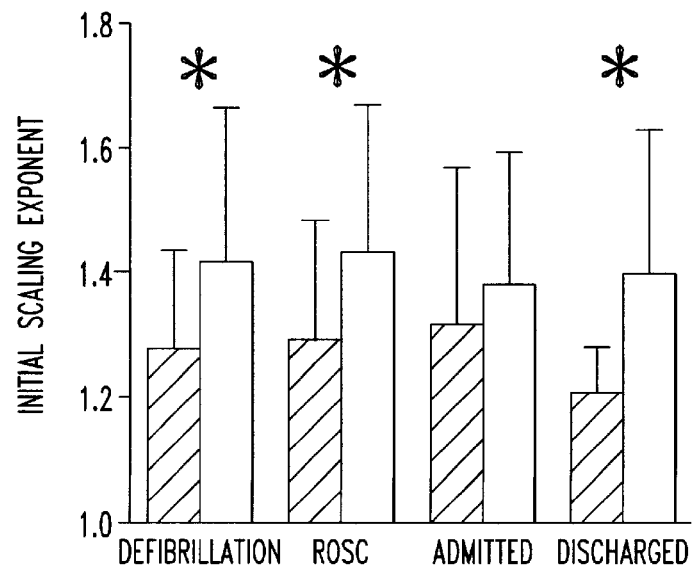
FIG. 8 is a plot of four bar charts of the mean (±SD) initial scaling exponents for favorable (left side of the bar chart) and unfavorable (right side of the bar chart) outcomes for defibrillation, return of spontaneous circulation (ROSC), admitted subjects, and discharged subjects.

Referring to FIG. 8, mean values for the scaling exponent are lower for groups with better clinical outcomes (i.e., left side of the bar charts). Better clinical response to therapy is associated with lower initial scaling exponents. The mean scaling exponent is lower for cases with successful AED defibrillation, ROSC, and survival to hospital discharge. Survival to hospital admission is not significantly associated with the scaling exponent (*, p<0.05), wherein the asterisk (*) indicates a statistically significant difference between the two groups with a significance level p<0.05. The scaling exponent differs between cases with successful and with failed AED defibrillation (t=2.94, df=73, 0=0.004), between cases with ROSC and with no ROSC (t=2.79, df=68.85, p=0.049), and between cases with survival to hospital discharge and with no survival (t=5.26, df=60.97, p<0.001). There is a trend towards lower scaling exponents in cases with survival to hospital admission compared to cases pronounced dead in the emergency department (t=1.02, df=66, p=0.059).

Figure 9A:
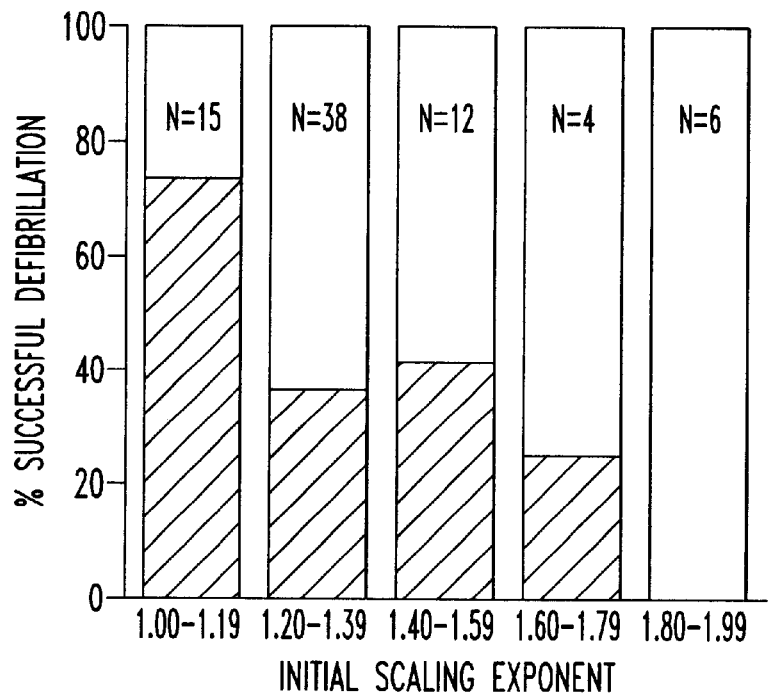
FIGS. 9A–9D are plots of survival percentages versus absolute values of the initial scaling exponents for patients who exhibit successful AED defibrillation, ROSC, survival to hospital admission, and survival to hospital discharge, respectively.
Figure 9B:
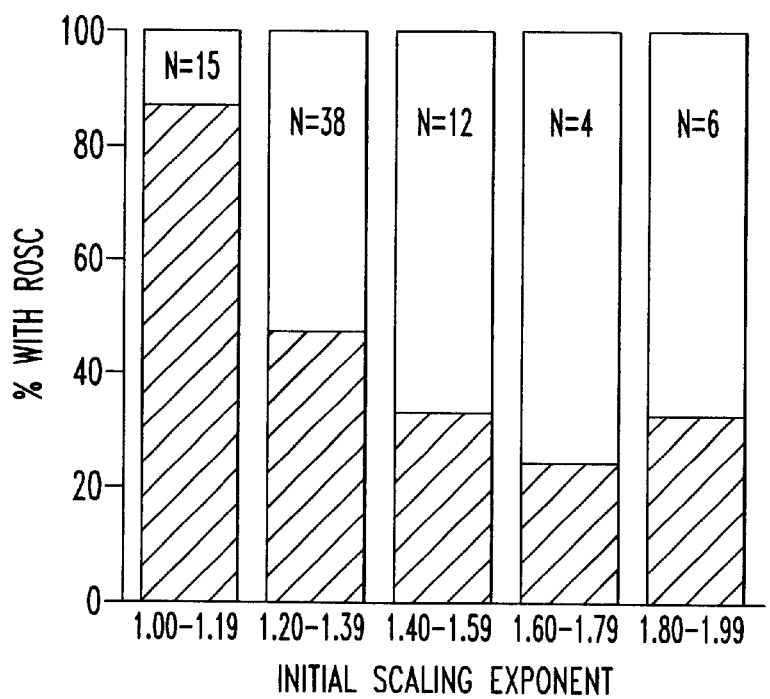
Figure 9C:
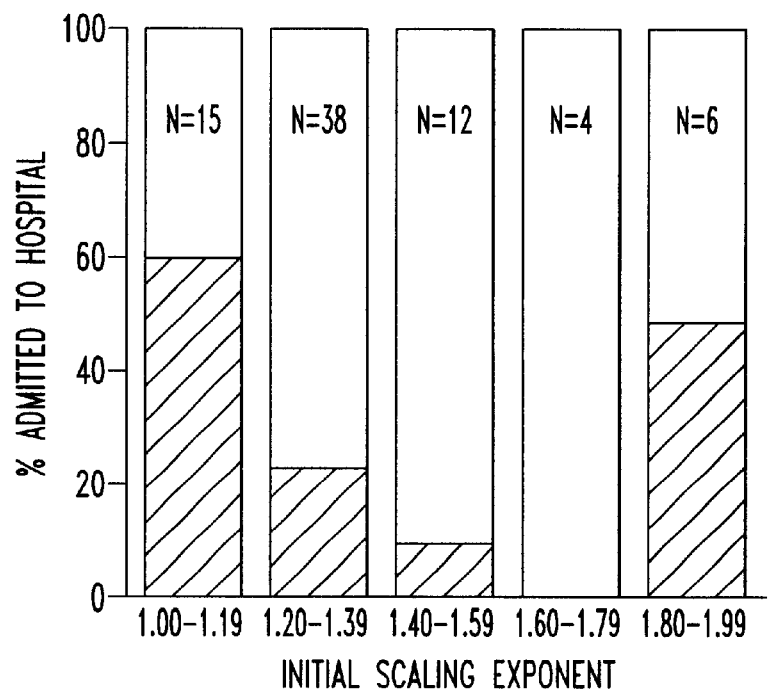
Figure 9D:
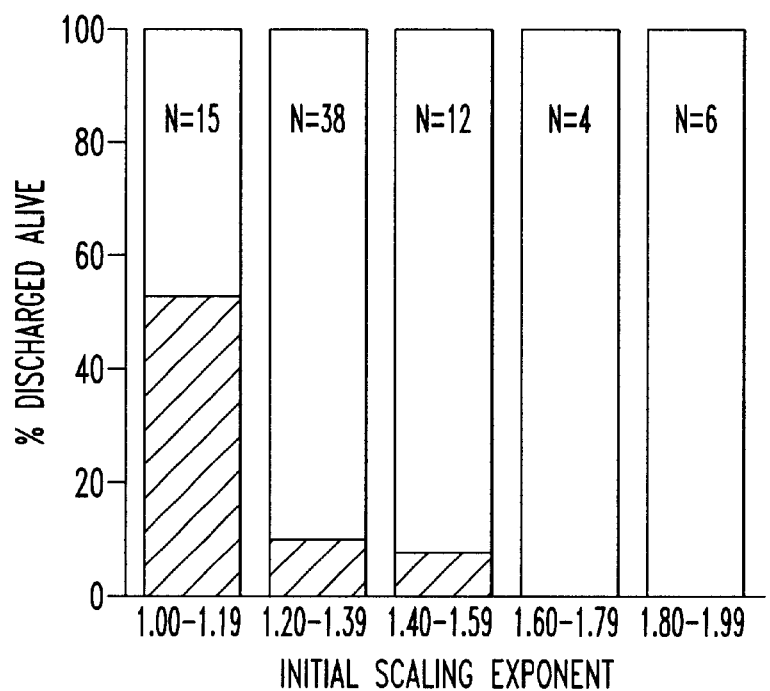

Lower values of the scaling exponent are associated within an increased probability of successful defibrillation as shown in FIGS. 9A–9D. These examples show that lower absolute values of the initial scaling exponent are associated with increased proportions of patients who exhibit: successful AED defibrillation (FIG. 9A), ROSC (FIG. 9B), survival to hospital admission (FIG. 9C), and survival to hospital discharge (FIG. 9D). The proportion of subjects successfully defibrillated by the AED is highest (73%) when the initial scaling exponent is in the range of 1.00–1.19 (Chi-square= 11.31, df=4, p=0.023). Furthermore, the initial value of the scaling exponent is related to the proportion of subjects who experienced ROSC (Chi-Square=11.16, df=4, p=0.025), who survived to hospital admission (Chi-square=11.23, df-4, p=0.024), and who survived to hospital discharge (Chi-square=17.57, df=4, p=0.0015).

Stepwise logistic regression identifies the scaling exponent and age as the only variables clearly associated with defibrillation success. The coefficient estimate (±SE) for the scaling exponent is 4.36±1.67 and for age is 0.046±0.022. Logistic regression identifies the scaling exponent as the only variable associated with ROSC, admission to the hospital, and survival to hospital discharge.

EXAMPLE 6

In order to confirm the incremental value of VF waveform analysis for predicting defibrillation success, a stepwise logistic regression model is examined in which all other candidate variables (e.g., age, sex, witnessed, bystander CPR, time from call receipt to paramedic arrival, and time from call receipt to shock) are forced into the model in the first step. The scaling exponent is then added in the second step resulting in a significant improvement in the −2 log likelihood of the model (improvement=6.10, df=5, p=0.0135).

Figure 10:
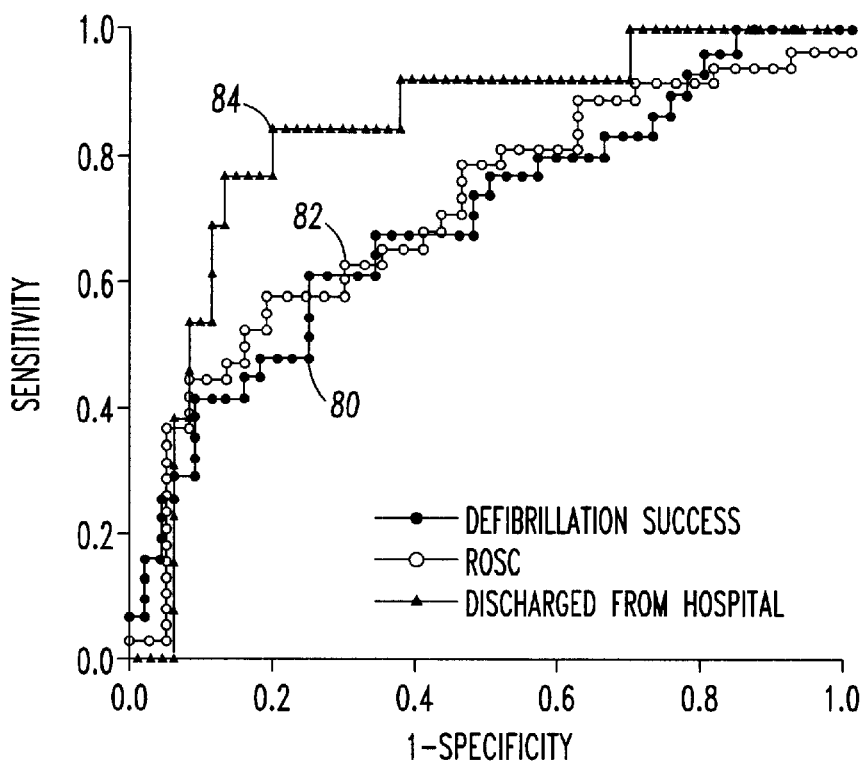
FIG. 10 is a plot of sensitivity for detecting all cases of successful defibrillation (i.e., proportion of true positives detected) versus 1-specificity (i.e., proportion of false positives detected) for receiver operator curves for the scaling exponent as a predictor of defibrillation success, ROSC, and survival to hospital discharge.

As shown in FIG. 10, receiver operator curves (ROC) are constructed to describe the utility of the scaling exponent by itself for predicting defibrillation success, ROSC, or discharge from the hospital. The three receiver operator curves 80,82,84 show the scaling exponent as a predictor of defibrillation success 80, ROSC 82, and survival to hospital discharge 84. Areas under these curves are 0.70, 0.71 and 0.84, respectively.

For comparison, the centroid frequency and root-mean-square amplitude are calculated from the same segments of VF. Centroid frequency is correlated with scaling exponent ($R^2$=0.204, F[1,73]=18.7, p<0.001). The areas under the ROC graphs (not shown) describing the utility of centroid frequency for predicting defibrillation success, ROSC, or discharge from the hospital are 0.53, 0.53 and 0.51, respectively.

The root-mean-square amplitude also is related to the scaling exponent. A semi-logarithmic relationship between these variables provides the best fit ($R^2$=0.788, F[1,73]=271.5, P<0.001). Consistent with the close relationship between amplitude and scaling exponent, the areas under the ROC graphs (not shown) indicate that amplitude could predict defibrillation success, ROSC, and discharge from the hospital. The areas under these graphs are 0.75, 0.71 and 0.84, respectively.

Multivariate regression using continuous variables identifies the time from call receipt to shock delivered as a covariate of the scaling exponent (partial correlation coefficient=0.444, p=0.001). Age is not associated with the value of the scaling exponent. The scaling exponent is lower in witnessed than in unwitnessed cases, as discussed below. However, neither the sex of the patient nor the presence of bystander CPR predicted the value of the scaling exponent.

Figure 11:
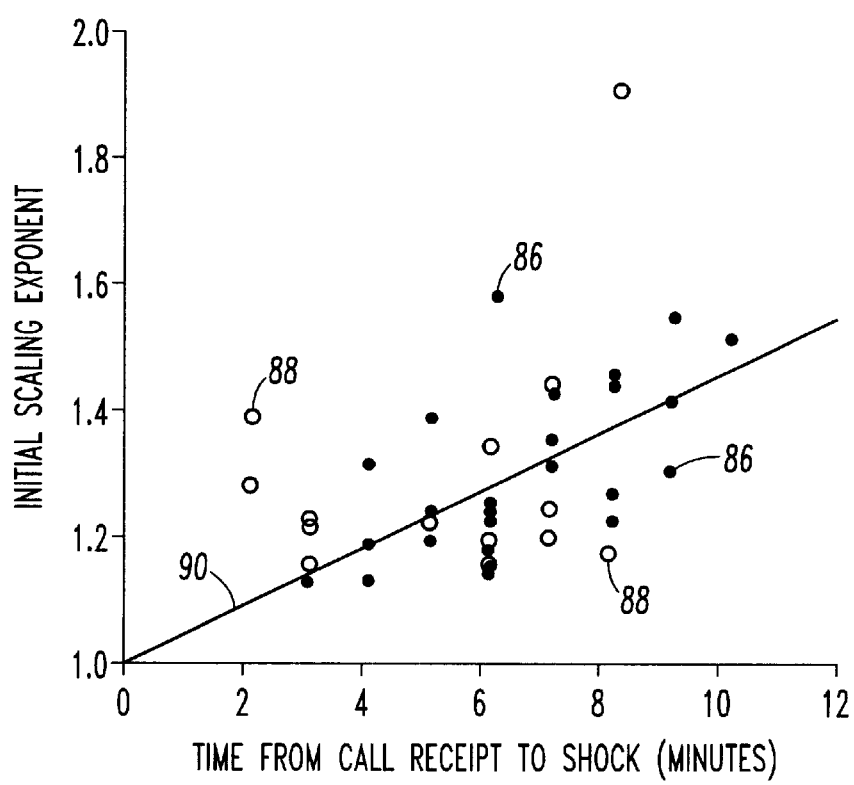
FIG. 11 is a plot of the initial scaling exponent versus time from call receipt to shock (in minutes), including a regression line for cases with no bystander CPR.

The scaling exponent increases with duration of untreated VF as shown in FIG. 11. Filled circles 86 represent cases with no bystander CPR, and open circles 88 represent cases with bystander CPR. The regression line 90 for cases with no bystander CPR is illustrated.

The scaling exponent is lower in cases with witnessed arrest (1.322±0.182, n=54) than in cases with unwitnessed arrest (1.461±0.281, n=21) (t=2.10, df=26.83, p=0.045). In witnessed arrests (n=45), where the time of emergency call receipt is a valid surrogate for the time of onset of VF, the interval from call receipt until first shock is positively correlated with scaling exponent ($R^2$=0.157, F[1,43]=8.01, p=0.007). Estimates of the time of first shock are not available for nine cases. In the subset of subjects with witnessed cardiac arrests and no bystander CPR (n=26), the association between interval from call receipt to first shock is associated more strongly with the increase in scaling exponent ($R^2$=0.383, F[1,24]=14.91, p=0.0007). Furthermore, the calculated rate of increase in scaling exponent for subjects with witnessed arrests and bystander CPR (slope=0.026, 95% CI [−0.023,0.074]) is less than the rate for subjects with witnessed arrests and no bystander CPR (slope=0.047, 95% CI [0.022,0.073]), although this difference does not reach statistical significance.

The foregoing examples illustrate the use of a measure derived from fractal geometry for the quantification of the VF waveform and prediction of response to defibrillation. This measure, the scaling exponent, is an estimate of the self-similarity dimension of the waveform. See Higuchi, T., *Physica D*, vol. 31, pp. 277–83. The scaling exponent provides a measure that is independent of the absolute amplitude of the recorded signal. Thus, the scaling exponent can be compared between recordings made using different equipment and different electrodes. For example, the present data confirm that the scaling exponent can be measured in human VF during OOHCA, and that it has similar magnitude and behavior in humans and swine.

It is believed that the present invention, which provides a method and apparatus for stratifying patients according to their probability of responding to standard treatment, will allow application of alternative algorithms (e.g., reperfusion and reoxygenation of the fibrillating heart in order to increase the probability of achieving an organized electrical activity after defibrillation; introducing a 90 s period of CPR prior to attempting defibrillation in order to improve survival in humans, especially where the delay prior to arrival of therapy exceeded four minutes) without delaying defibrillation for patients in whom it is likely to succeed. In particular, the scaling exponent described herein may be a correlate of the elapsed ischemic interval prior to attempting defibrillation (see FIG. 11). Although the sensitivity of this measure for identifying cases for which defibrillation will be successful may not justify withholding defibrillation altogether, knowledge of the probability of success prior to defibrillation could help guide the timing or energy of electrical therapy. For example, subjects with prolonged VF and high scaling exponents may benefit from brief periods of artificial perfusion prior to electrical therapy. Cobb, L., et al., *JAMA,* 1999, vol. 281, pp. 1182–88.

Nonlinear dynamical measures, such as the fractal dimension, are more appropriate than amplitude and frequency measures for quantifying a non-periodic waveform like VF. In fact, complex dynamical behavior has been described in several models of VF. Witkowski, F., et al., Spatiotemporal evolution of ventricular fibrillation, *Nature,* 1998, vol. 392, pp. 78–82; Gray, R., et al., Spatial and temporal organization during cardiac fibrillation, *Nature,* 1998, vol. 392, pp. 75–78. Furthermore, measurements based upon nonlinear dynamics have previously been developed for the VF waveform in stabilized animal preparations. Hastings, H., et al., Nonlinear dynamics in ventricular fibrillation, *Proceedings of the National Academy of Sciences, USA,* 1996, vol. 93, pp. 10496–99. In the clinical setting and in unperfused animals, VF waveform does not exhibit true fractal structure, because it has scaling relationships and self-similarity only over a limited range of timescales (see FIGS. 6A–6D), Kaplan, D., et al., Is fibrillation chaos?, *Circulation Research,* 1990, vol. 67, pp. 886–92, and because it is not stationary over time. Nevertheless, measures of fractal dimension over limited ranges have proven useful for characterizing many natural phenomena. Avnir, D., et al., Is the geometry of nature fractal?, *Science,* 1998, vol. 279, pp. 39–40. The scaling exponent uniquely distinguishes early and late VF and does not differ according to the absolute amplitude of the waveform. Thus, this measure can be compared between different recording conditions and even between different studies.

The examples disclosed herein suggest that the structure of the human VF waveform evolves over time (see FIG. 11). A similar increase in the scaling exponent over time is observed in swine. Conceptually, the scaling exponent distinguishes coarse VF (low scaling exponent) from fine VF (high scaling exponent). An alternative interpretation is that low values of the scaling exponent reflect more large-scale structure in the VF waveform, whereas high values of the scaling exponent reflect less large-scale structure. Previous investigations in dogs suggest that a stronger correlation between the time of depolarization in spatially separated parts of the myocardium is associated with a greater likelihood of successful defibrillation. Hsia, P-W., et al., Defibrillation success is associated with myocardial organization: spatial coherence as a new method of quantifying the electrical organization of the heart, *Journal of Electrocardiology,* 1996, vol. 29 (Supp.), pp. 189–97. Furthermore, the correlation between electrical depolarization in spatially separated pieces of myocardium decreases over time. Witkowski, F., et al., *Nature,* 1998, vol. 392, pp. 78–82. It is possible that the scaling exponent is a macroscopic measure of the spatial and temporal correlation of myocardial depolarization. Consequently, relatively lower scaling exponents are associated with a greater likelihood of successful defibrillation (see FIGS. 8 and 9A–9D). Taken together, these data suggest that analyses of VF waveform provide some insight into the physiological state of the subject, which is perhaps related to the total duration of ischemia.

The exemplary methods for ECG analysis may also be applied to better distinguish VF from other rhythms in automated defibrillators. Furthermore, these techniques might have predictive value for the response to therapy in other aperiodic dysrhythmias such as atrial fibrillation.

Human VF exhibits a time-dependent structure that can be quantified using the amplitude-independent fractal self-similarity dimension. This scaling exponent is an estimate of the fractal dimension. Over time, the scaling exponent increases reflecting a loss of structure in the VF waveform. Moreover, the absolute value of the scaling exponent predicts the likelihood of successful defibrillation and ultimate survival. Even with consideration of other potential factors that may influence resuscitation, this tool remains predictive and, thus, it is believed that it provides utility in guiding future therapeutic trials.

The application of nonlinear dynamics to ECG analysis is different from prior techniques that rely on frequency spectral analyses. Prior analyses are described using fast Fourier transforms and wavelet analyses. However, the actual ECG waveform during VF is not periodic, and is more correctly approached using nonlinear techniques. The exemplary system and method provides a caregiver with a quantitative descriptor of the ECG waveform during resuscitation attempts.

The retrospectively analyzed human data suggests that certain interventions, such as chest compressions, ventilation and drug administration, may improve the VF waveform, and that other interventions, such as failed defibrillation, can worsen the ECG waveform. The current data supports the use of the scaling exponent for on-line monitoring of the response to therapy during resuscitation, and for automatically and/or manually guiding defibrillation and/or alternative therapies while treating dysrhythmias.

Other applications of the scaling exponent method and apparatus disclosed herein include: (1) analyzing structure in wide-complex tachycardia such as ventricular tachycardia; (2) examining structure in other ventricular dysrhythmias (e.g., torsades-de-pointes, accelerated idioventricular rhythms); (3) distinguishing periodic (e.g., sinus rhythm, 60 Hz noise) from aperiodic (e.g., VF, torsades-de-pointes, asystole) ECG signals by looking at the linearity of the function in different domains of the lag k in connection with step 46 of FIG. 7A; and (4) characterizing the signal to noise ratio of the ECG signal (because increasing background white noise while holding the ECG signal constant skews the scaling exponent towards 2.0).

Defibrillators are also employed for non-human research applications. Accordingly, the scaling exponent may be employed to describe drug or electricity-induced VF in an animal in order to confirm that the animal model may be directly compared to human disease (i.e., if the human and animal exponents are the same, then it provides for the argument that the animal is a good model).

While other algorithms for estimating the fractal dimension of the VF waveform can be employed, the scaling exponent offers computational simplicity that allows it to be implemented in real-time.

While for clarity of disclosure reference has been made herein to a display 34 for displaying the scaling exponent and other information, it will be appreciated that such information may be stored, printed on hard copy, be computer modified, or be combined with other data. All such processing shall be deemed to fall within the terms "display" or "displaying" as employed herein.

While reference has been made to the exemplary microprocessor 18, other suitable controllers, processors or computers such as, for example, microcomputers, PCs, workstations, minicomputers or mainframe computers may be employed.

Whereas particular embodiments of the present invention have been described above for purposes of illustration, it will be appreciated by those skilled in the art that numerous variations in the details may be made without departing from the invention as described in the claims which are appended hereto.

We claim:

1. A defibrillator for selectively delivering a defibrillation pulse to a patient, said defibrillator comprising:

electrodes adapted for placement on the patient;

a monitoring circuit for providing an electrocardiogram (ECG) of the patient;

a defibrillation pulse generator including an energy store for delivering a defibrillation pulse;

a switch in electrical communication with the monitoring circuit and the defibrillation pulse generator for selectively electrically connecting the monitoring circuit and the defibrillation pulse generator to the electrodes; and a control system in electrical communication with the monitoring circuit, the defibrillation pulse generator, and the switch, said control system comprising means for:
(i) causing the switch to electrically connect the monitoring circuit to the electrodes in order to provide the ECG of the patient,
(ii) determining a scaling exponent for the patient from the ECG thereof, and
(iii) comparing the scaling exponent to a predetermined value and selectively causing the switch to electrically connect the defibrillation pulse generator to the electrodes in order that the energy store delivers the defibrillation pulse to the patient.

2. The defibrillator of claim 1, wherein said control system includes a display operatively associated therewith for displaying the scaling exponent.

3. The defibrillator of claim 1, wherein said control system includes a non-volatile memory for storing the predetermined value.

4. The defibrillator of claim 1, wherein said control system includes an input for entering the predetermined value.

5. A defibrillator for selectively delivering a defibrillation pulse to a patient, said defibrillator comprising:

electrodes adapted for placement on the patient;

a monitoring circuit for providing an electrocardiogram (ECG) of the patient;

a defibrillation pulse generator including an energy store for delivering a defibrillation pulse;

a switch in electrical communication with the monitoring circuit and the defibrillation pulse generator for selectively electrically connecting the monitoring circuit and the defibrillation pulse generator to the electrodes; and a control system in electrical communication with the monitoring circuit, the defibrillation pulse generator, and the switch for:
(i) causing the switch to electrically connect the monitoring circuit to the electrodes in order to provide the ECG of the patient,
(ii) determining a scaling exponent for the patient from the ECG thereof, and
(iii) comparing the scaling exponent to a predetermined value and selectively causing the switch to electrically connect the defibrillation pulse generator to the electrodes in order that the energy store delivers the defibrillation pulse to the patient, wherein said control system includes means for adjusting the predetermined value.

6. A defibrillator for selectively delivering a defibrillation pulse to a patient, said defibrillator comprising:

electrodes adapted for placement on the patient;

a monitoring circuit for providing an electrocardiogram (ECG) of the patient;

a defibrillation pulse generator including an energy store for delivering a defibrillation pulse;

a switch in electrical communication with the monitoring circuit and the defibrillation pulse generator for selectively electrically connecting the monitoring circuit and the defibrillation pulse generator to the electrodes; and a control system in electrical communication with the monitoring circuit, the defibrillation pulse generator, and the switch, said control system comprising means for:
(i) causing the switch to electrically connect the monitoring circuit to the electrodes in order to take the ECG of the patient,
(ii) determining a scaling exponent for the patient from the ECG thereof,
(iii) displaying the scaling exponent, and
(iv) receiving an input responsive to said displaying and selectively causing the switch to electrically connect the defibrillation pulse generator to the electrodes in order that the energy store delivers the defibrillation pulse to the patient.

7. A method of selectively delivering a defibrillation pulse to a patient comprising the steps of:

placing electrodes on the patient;

taking an electrocardiogram (ECG) of the patient;

determining a scaling exponent for the patient from the ECG thereof;

comparing the scaling exponent to a predetermined value; and selectively delivering a defibrillation pulse through the electrodes to the patient based upon said comparing step.

8. The method of claim 7 further comprising:

employing about 1.3 as said predetermined value;

comparing the scaling exponent to said predetermined value of about 1.3; and selectively delivering the defibrillation pulse when the scaling exponent is less than said predetermined value of about 1.3.

9. The method of claim 7 further comprising:

delivering another defibrillation pulse after said step of selectively delivering a defibrillation pulse.

10. The method of claim 7 further comprising:

manually overriding said steps of taking an ECG, determining a scaling exponent, comparing the scaling exponent, and selectively delivering a defibrillation pulse; and manually initiating delivery of a defibrillation pulse.

11. The method of claim 7 further comprising:

employing a human being as said patient.

12. The method of claim 7 further comprising:

employing a member of the animal kingdom as said patient.

13. The method of claim 7 further comprising:

employing said steps of taking an ECG, determining a scaling exponent, comparing the scaling exponent, and selectively delivering a defibrillation pulse in real time.

14. The method of claim 7 further comprising:
displaying the scaling exponent.

15. The method of claim 7 further comprising:
selectively delivering the defibrillation pulse to the patient when the scaling exponent is less than the predetermined value.

16. The method of claim 15 further comprising:
employing about 1.3 as said predetermined value.

17. The method of claim 7 further comprising:
selectively displaying a suggested alternative therapy when the scaling exponent is greater than the predetermined value.

18. The method of claim 17 further comprising:
employing about 1.3 as said predetermined value.

19. The method of claim 7 further comprising:
selectively displaying a suggested alternative therapy for the patient when the scaling exponent is greater than said predetermined value.

20. The method of claim 19 further comprising:
employing reperfusion as said suggested alternative therapy.

21. The method of claim 19 further comprising:
employing as said suggested alternative therapy:
reoxygenating a fibrillating heart of the patient; and
employing defibrillation after said reoxygenating step.

22. The method of claim 19 further comprising:
employing as said suggested alternative therapy:
employing artificial perfusion; and
employing defibrillation after said employing artificial perfusion step.

23. The method of claim 19 further comprising:
employing a period of cardiopulmonary resuscitation (CPR) as said suggested alternative therapy.

24. The method of claim 23 further comprising:
employing defibrillation after said period of CPR.

25. The method of claim 19 further comprising:
employing at least one of cardiopulmonary resuscitation (CPR) and ventilating the patient as said suggested alternative therapy.

26. The method of claim 25 further comprising:
employing defibrillation after said at least one of said CPR and said ventilating the patient.

27. The method of claim 7 further comprising:
expressing said ECG as series of a plurality of voltage measurements.

28. The method of claim 27 further comprising:
varying a lag from: (a) a difference between adjacent pairs of said voltage measurements to (b) a difference between each N-th pair of said voltage measurements.

29. The method of claim 28 further comprising:
employing k as said lag;
employing i as an index of said voltage measurements;
employing X(i) as one of said voltage measurements;
employing X(i+k) as another one of said voltage measurements;
calculating a sum of absolute potential differences between each i-th measurement of said ECG, X(i), and each (i+k)-th measurement of said ECG, X(i+k).

30. The method of claim 29 further comprising:
employing M as a count of said voltage measurements;
normalizing said sum for each value of said lag, k, by a factor, [M/k(M−k)]; and
defining a function, L(k), as said sum:

$$L(k) = M/(k(M-k)) \times \sum_{i=1}^{M-k} |X(i) - X(i+k)|.$$

31. The method of claim 28 further comprising:
employing d as the scaling exponent; and
fitting values of said function, L(k), to an exponential function in order to describe a scaling relationship between said function, L(k), and said lag, k:

$$L(k) = k^{(1-d)}.$$

32. The method of claim 31 further comprising:
employing said function, L(k), with a plateau in a region centered between about k=5 and about k=20;
defining a plurality of regions, each of which has about five values of said function, L(k);
calculating a plurality of slopes of said function, L(k), for each of said regions centered between about k=5 and about k=20; and
identifying an inflection point of said function, L(k), from a maximum one of said slopes.

33. The method of claim 32 further comprising:
employing a plurality of points centered around said inflection point; and
fitting a slope of a least-squares line to a log-log plot of said function, L(k).

34. The method of claim 33 further comprising:
calculating the scaling exponent, d, from said slope of a least-squares line.

35. The method of claim 30 further comprising:
employing about 2048 as said count, M, of said voltage measurements.

36. The method of claim 35 further comprising:
measuring said voltage measurements at a rate of about 400 measurements per second.

37. A method of diagnosing and treating a patient comprising the steps of:
placing electrodes on the patient;
taking an electrocardiogram (ECG) of the patient;
determining a scaling exponent for the patient from the ECG thereof;
displaying the scaling exponent;
receiving an input responsive to said step of displaying the scaling exponent; and
selectively defibrillating the patient responsive to said receiving step.

38. The method of claim 37 further comprising:
employing an input from an operator as said input responsive to said step of displaying the scaling exponent.

* * * * *

UNITED STATES PATENT AND TRADEMARK OFFICE
CERTIFICATE OF CORRECTION

PATENT NO.    : 6,438,419 B1
DATED         : August 20, 2002
INVENTOR(S)   : Clifton W. Callaway et al.

It is certified that error appears in the above-identified patent and that said Letters Patent is hereby corrected as shown below:

Column 1,
Line 41, "a priori" should read -- *a priori* --.

Column 8,
Line 6, delete the word "can".

Signed and Sealed this

Twenty-fourth Day of December, 2002

JAMES E. ROGAN
*Director of the United States Patent and Trademark Office*

UNITED STATES PATENT AND TRADEMARK OFFICE
Certificate

Patent No. 6,438,419 B1                                                                     Patented: August 20, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Clifton W. Callaway, Pittsburgh, PA (US); Lawrence D. Sherman, Aspinwall, PA (US); James J. Menegazzi, Pittsburgh, PA (US)

Signed and Sealed this Fifth Day of April 2011.

Niketa I. Patel
*Supervisory Patent Examiner*
Art Unit 3762
Technology Center 3700